US008781585B2

(12) United States Patent
Gunderson et al.

(10) Patent No.: US 8,781,585 B2
(45) Date of Patent: *Jul. 15, 2014

(54) IDENTIFICATION AND REMEDIATION OF OVERSENSED CARDIAC EVENTS USING FAR-FIELD ELECTROGRAMS

(75) Inventors: Bruce D. Gunderson, Plymouth, MN (US); Donald James Ruzin, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/301,619

(22) Filed: Nov. 21, 2011

(65) Prior Publication Data

US 2012/0071944 A1 Mar. 22, 2012

Related U.S. Application Data

(63) Continuation of application No. 12/260,560, filed on Oct. 29, 2008, now Pat. No. 8,078,277.

(51) Int. Cl.
*A61N 1/00* (2006.01)
(52) U.S. Cl.
USPC ............................................. 607/27; 607/28
(58) Field of Classification Search
USPC ..................................................... 607/27, 28
See application file for complete search history.

(56) References Cited

U.S. PATENT DOCUMENTS

| 4,140,131 A | 2/1979 | Dutcher et al. |
| 4,332,256 A | 6/1982 | Brownlee et al. |
| 4,374,382 A | 2/1983 | Markowitz |
| 4,428,378 A | 1/1984 | Anderson et al. |
| 4,549,548 A | 10/1985 | Wittkampf et al. |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,201,865 A | 4/1993 | Kuehn |
| 5,215,081 A | 6/1993 | Ostroff |
| 5,224,475 A | 7/1993 | Berg et al. |

(Continued)

OTHER PUBLICATIONS (PCT/US2009/060351) PCT Notification of Transmittal of the International Search Report and the Written Opinion of the International Searching Authority.

*Primary Examiner* — Michael Kahelin
*Assistant Examiner* — Mallika D Fairchild
(74) *Attorney, Agent, or Firm* — Michael C. Soldner

(57) ABSTRACT

In general, the disclosure is directed to techniques for identification and remediation of oversensed cardiac events using far-field electrograms (FFEGMs). Identification of oversensed cardiac events can be used in an ICD to prevent ventricular fibrillation (VF) detection, and thereby avoid delivery of an unnecessary defibrillation shock. Alternatively, or additionally, identification of oversensed cardiac events can be used in an ICD to support delivery of bradycardia pacing during an oversensing condition. In some cases, bradycardia pacing delivered in response to detection of oversensed cardiac events may include pacing pulses from multiple vectors to provide redundancy in the event the oversensing may be due to a lead-related condition.

39 Claims, 11 Drawing Sheets

(56) References Cited

U.S. PATENT DOCUMENTS

| | | |
|---|---|---|
| 5,226,415 A | 7/1993 | Girodo et al. |
| 5,292,343 A | 3/1994 | Blanchette et al. |
| 5,312,441 A | 5/1994 | Mader et al. |
| 5,314,450 A | 5/1994 | Thompson |
| 5,324,315 A | 6/1994 | Grevious |
| 5,354,319 A | 10/1994 | Wyborny et al. |
| 5,381,803 A | 1/1995 | Herleikson et al. |
| 5,383,909 A | 1/1995 | Keimel |
| 5,411,530 A | 5/1995 | Akhtar |
| 5,431,692 A | 7/1995 | Hansen et al. |
| 5,462,060 A | 10/1995 | Jacobson et al. |
| 5,507,746 A | 4/1996 | Lin |
| 5,507,786 A | 4/1996 | Morgan et al. |
| 5,534,018 A | 7/1996 | Wahlstrand et al. |
| 5,545,183 A | 8/1996 | Altman |
| 5,545,186 A | 8/1996 | Olson et al. |
| 5,549,646 A | 8/1996 | Katz et al. |
| 5,558,098 A | 9/1996 | Fain |
| 5,564,434 A | 10/1996 | Halperin et al. |
| 5,660,183 A | 8/1997 | Chiang et al. |
| 5,707,398 A | 1/1998 | Lu |
| 5,722,997 A | 3/1998 | Nedungadi et al. |
| 5,730,141 A | 3/1998 | Fain et al. |
| 5,741,311 A | 4/1998 | McVenes et al. |
| 5,755,735 A | 5/1998 | Richter et al. |
| 5,755,736 A | 5/1998 | Gillberg et al. |
| 5,755,742 A | 5/1998 | Schuelke et al. |
| 5,776,168 A | 7/1998 | Gunderson |
| 5,814,088 A | 9/1998 | Paul et al. |
| 5,868,793 A | 2/1999 | Nitzsche et al. |
| 5,891,170 A | 4/1999 | Nitzsche et al. |
| 5,891,179 A | 4/1999 | Er et al. |
| 5,897,577 A | 4/1999 | Cinbis et al. |
| 5,910,156 A | 6/1999 | Cinbis et al. |
| 5,944,746 A | 8/1999 | Kroll |
| 6,067,473 A | 5/2000 | Greeninger et al. |
| 6,070,097 A | 5/2000 | Kreger et al. |
| 6,085,118 A | 7/2000 | Hirschberg et al. |
| 6,112,119 A | 8/2000 | Schuelke et al. |
| 6,129,746 A | 10/2000 | Levine et al. |
| 6,141,585 A | 10/2000 | Prutchi et al. |
| 6,155,267 A | 12/2000 | Nelson |
| 6,169,923 B1 | 1/2001 | Kroll |
| 6,266,554 B1 | 7/2001 | Hsu et al. |
| 6,317,632 B1 | 11/2001 | Krig et al. |
| 6,317,633 B1 | 11/2001 | Jorgenson et al. |
| 6,321,115 B1 | 11/2001 | Mouchawar et al. |
| 6,393,316 B1 | 5/2002 | Gillberg et al. |
| 6,434,428 B1 | 8/2002 | Sloman et al. |
| 6,445,952 B1 | 9/2002 | Manrodt et al. |
| 6,477,417 B1 | 11/2002 | Levine |
| 6,493,584 B1 | 12/2002 | Lu |
| 6,493,586 B1 | 12/2002 | Stahmann et al. |
| 6,629,931 B1 | 10/2003 | Begemann et al. |
| 6,650,931 B1 | 11/2003 | McClure et al. |
| 6,658,294 B1 | 12/2003 | Zadeh et al. |
| 6,721,600 B2 | 4/2004 | Jorgenson et al. |
| 6,760,624 B2 | 7/2004 | Anderson et al. |
| 6,788,971 B1 | 9/2004 | Sloman et al. |
| 6,865,141 B2 | 3/2005 | Tada et al. |
| 7,027,856 B2 | 4/2006 | Zhou et al. |
| 7,047,083 B2 | 5/2006 | Gunderson et al. |
| 7,082,328 B2 | 7/2006 | Funke |
| 7,167,747 B2 | 1/2007 | Gunderson et al. |
| 7,231,251 B2 | 6/2007 | Yonce et al. |
| 7,236,828 B2 | 6/2007 | Casavant et al. |
| 7,266,409 B2 | 9/2007 | Gunderson |
| 7,289,851 B2 | 10/2007 | Gunderson et al. |
| 7,333,855 B2 | 2/2008 | Gunderson et al. |
| 7,369,893 B2 | 5/2008 | Gunderson |
| 7,539,540 B2 | 5/2009 | Gunderson et al. |
| 7,567,835 B2 | 7/2009 | Gunderson et al. |
| 2001/0031997 A1 | 10/2001 | Lee |
| 2001/0037366 A1 | 11/2001 | Webb et al. |
| 2002/0091333 A1 | 7/2002 | Hsu et al. |
| 2002/0116031 A1 | 8/2002 | Vonk |
| 2002/0118215 A1 | 8/2002 | Ball et al. |
| 2002/0120307 A1 | 8/2002 | Jorgenson et al. |
| 2003/0074026 A1 | 4/2003 | Thompson et al. |
| 2003/0204215 A1 | 10/2003 | Gunderson et al. |
| 2004/0015197 A1 | 1/2004 | Gunderson |
| 2004/0088018 A1 | 5/2004 | Sawchuk et al. |
| 2004/0106955 A1 | 6/2004 | Swerdlow et al. |
| 2004/0122487 A1 | 6/2004 | Hatlestad et al. |
| 2004/0186388 A1 | 9/2004 | Gerasimov |
| 2004/0220631 A1 | 11/2004 | Burnes et al. |
| 2004/0230233 A1 | 11/2004 | Gunderson et al. |
| 2004/0230242 A1 | 11/2004 | van Dam et al. |
| 2005/0137636 A1 | 6/2005 | Gunderson et al. |
| 2005/0154421 A1* | 7/2005 | Ousdigian ................ 607/14 |
| 2005/0159785 A1 | 7/2005 | Rueter |
| 2006/0074454 A1 | 4/2006 | Freeberg |
| 2006/0116730 A1 | 6/2006 | Gunderson |
| 2006/0235476 A1 | 10/2006 | Gunderson et al. |
| 2006/0264777 A1 | 11/2006 | Drew |
| 2008/0082012 A1 | 4/2008 | Gunderson et al. |
| 2008/0082014 A1 | 4/2008 | Cao |
| 2008/0161870 A1 | 7/2008 | Gunderson |
| 2008/0161872 A1 | 7/2008 | Gunderson |
| 2008/0172098 A1 | 7/2008 | Gunderson |
| 2010/0106209 A1 | 4/2010 | Gunderson et al. |

* cited by examiner

IDENTIFICATION AND REMEDIATION OF OVERSENSED CARDIAC EVENTS USING FAR-FIELD ELECTROGRAMS

This application is a continuation of U.S. patent application Ser. No. 12/260,560, entitled "IDENTIFICATION AND REMEDIATION OF OVERSENSED CARDIAC EVENTS USING FAR-FIELD ELECTROGRAMS," filed on Oct. 29, 2008, the entire content of which is incorporated herein by reference.

TECHNICAL FIELD

The disclosure relates to implantable medical devices (IMDs), and, more particularly, to detection of oversensed cardiac events by implantable medical devices.

BACKGROUND

A variety of implantable medical devices (IMDs) for delivering a therapy have been clinically implanted or proposed for clinical implantation in patients. Some implantable medical devices may employ one or more elongated electrical leads carrying stimulation electrodes, sense electrodes, and/or other sensors. Implantable medical devices may deliver therapy or monitor conditions with respect to a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter-defibrillators (ICDs), provide therapeutic electrical stimulation to the heart via electrodes carried by one or more implantable leads. The electrical stimulation may include signals such as pacing pulses, cardioversion shocks, or defibrillation shocks to address abnormal cardiac rhythms such as bradycardia, tachycardia, or fibrillation. In some cases, an IMD may sense intrinsic depolarizations of the heart to identify normal or abnormal rhythms. Upon detection of an abnormal rhythm, the device may deliver an appropriate electrical stimulation signal or signals to restore or maintain a more normal rhythm. For example, in some cases, an IMD may deliver pacing pulses to the heart upon detecting tachycardia or bradycardia, and deliver cardioversion or defibrillation shocks to the heart upon detecting tachycardia or fibrillation.

Leads associated with an IMD typically include a lead body containing one or more elongated electrical conductors that extend through the lead body from a connector assembly provided at a proximal lead end to one or more electrodes located at the distal lead end or elsewhere along the length of the lead body. The conductors connect stimulation and/or sensing circuitry within an associated IMD housing to respective electrodes or sensors. Some electrodes may be used for both stimulation and sensing, while other electrodes may be dedicated to only stimulation or only sensing. Each electrical conductor is typically electrically isolated from other electrical conductors, and is encased within an outer sheath that electrically insulates the lead conductors from body tissue and fluids.

Cardiac lead bodies tend to be continuously flexed by the beating of the heart. Other stresses may be applied to the lead body during implantation or lead repositioning. Patient movement can cause the route traversed by the lead body to be constricted or otherwise altered, causing stresses on the lead body. The electrical connection between implantable medical device connector elements and the lead connector elements can be intermittently or continuously disrupted. Connection mechanisms, such as set screws, may be insufficiently tightened at the time of implantation, followed by a gradual loosening of the connection. Also, lead pins may not be completely inserted. In some cases, changes in leads or connections may result in intermittent or continuous changes in lead impedance.

Short circuits, open circuits or significant changes in impedance may be referred to, in general, as lead-related conditions. In the case of cardiac leads, sensing of an intrinsic heart rhythm through a lead can be altered by lead-related conditions. Structural modifications to leads, conductors or electrodes may alter sensing integrity. Furthermore, impedance changes in the stimulation path due to lead-related conditions may affect sensing and stimulation integrity for pacing, cardioversion, or defibrillation. In addition to lead-related conditions, conditions associated with sensor devices or sensing circuitry, as well as conditions associated with electrodes or sensors not located on leads, may affect sensing integrity. Lead-related conditions, electromagnetic interference (EMI), myopotentials caused by patient movement, or other noise sources may affect sensing integrity. Cardiac events that are falsely detected may be referred to as oversensed cardiac events.

SUMMARY

In general, the disclosure is directed to techniques for identification and remediation of oversensed cardiac events in an IMD. The techniques may make use of far-field electrograms (FFEGMs) to identify oversensed cardiac events. Identification of oversensed cardiac events can be used in an IMD to prevent inappropriate ventricular fibrillation (VF) detection, and thereby avoid delivery of an unnecessary defibrillation shock. Alternatively, or additionally, identification of oversensed cardiac events can be used in an IMD to support delivery of bradycardia pacing during an oversensing condition. In some cases, bradycardia pacing delivered in response to detection of oversensed cardiac events may include pacing pulses from multiple stimulation vectors to provide redundancy in the event the oversensing may be due to a lead-related condition. The techniques, in some cases, may repair interval data upon identification of oversensing to support proper operation of defibrillation and/or pacing therapies that are responsive to the interval data.

In one example, the disclosure provides a method comprising acquiring a first cardiac signal via a first sense electrode configuration, acquiring a second cardiac signal via a second sense electrode configuration, detecting cardiac events in the first cardiac signal, identifying at least some of the cardiac events detected in the first cardiac signal as oversensed events based on whether one or more characteristics of the second cardiac signal confirm the cardiac events, and controlling delivery of cardiac electrical stimulation therapy to a patient based on the identification of the oversensed events.

In another example, the disclosure provides an implantable medical device comprising an electrical sensing module configured to acquire first cardiac signal via a first sense electrode configuration, and acquire a second cardiac signal via a second sense electrode configuration, a stimulation module configured to deliver cardiac electrical stimulation therapy to a patient via stimulation electrodes, and a processor configured to detect cardiac events in the first cardiac signal, identify at least some of the cardiac events detected in the first cardiac signal as oversensed events based on whether one or more characteristics of the second cardiac signal confirm the cardiac events, and control the stimulation module to deliver the cardiac electrical stimulation therapy to the patient based on the identification of the oversensed events.

In another example, the disclosure provides a computer-readable storage medium comprising instructions that, when executed by a processor in an implantable medical device, cause the processor to detect cardiac events in a first cardiac signal acquired via a first sense electrode configuration, identify at least some of the cardiac events detected in the first cardiac signal as oversensed events based on whether one or more characteristics of a second cardiac signal acquired via a second sense electrode configuration confirm the cardiac events, and control a stimulation module to deliver of cardiac electrical stimulation therapy to a patient based on the identification of the oversensed events.

The details of one or more aspects of the disclosure are set forth in the accompanying drawings and the description below. Other features, objects, and advantages will be apparent from the description and drawings, and from the claims.

DETAILED DESCRIPTION

Figure 1:
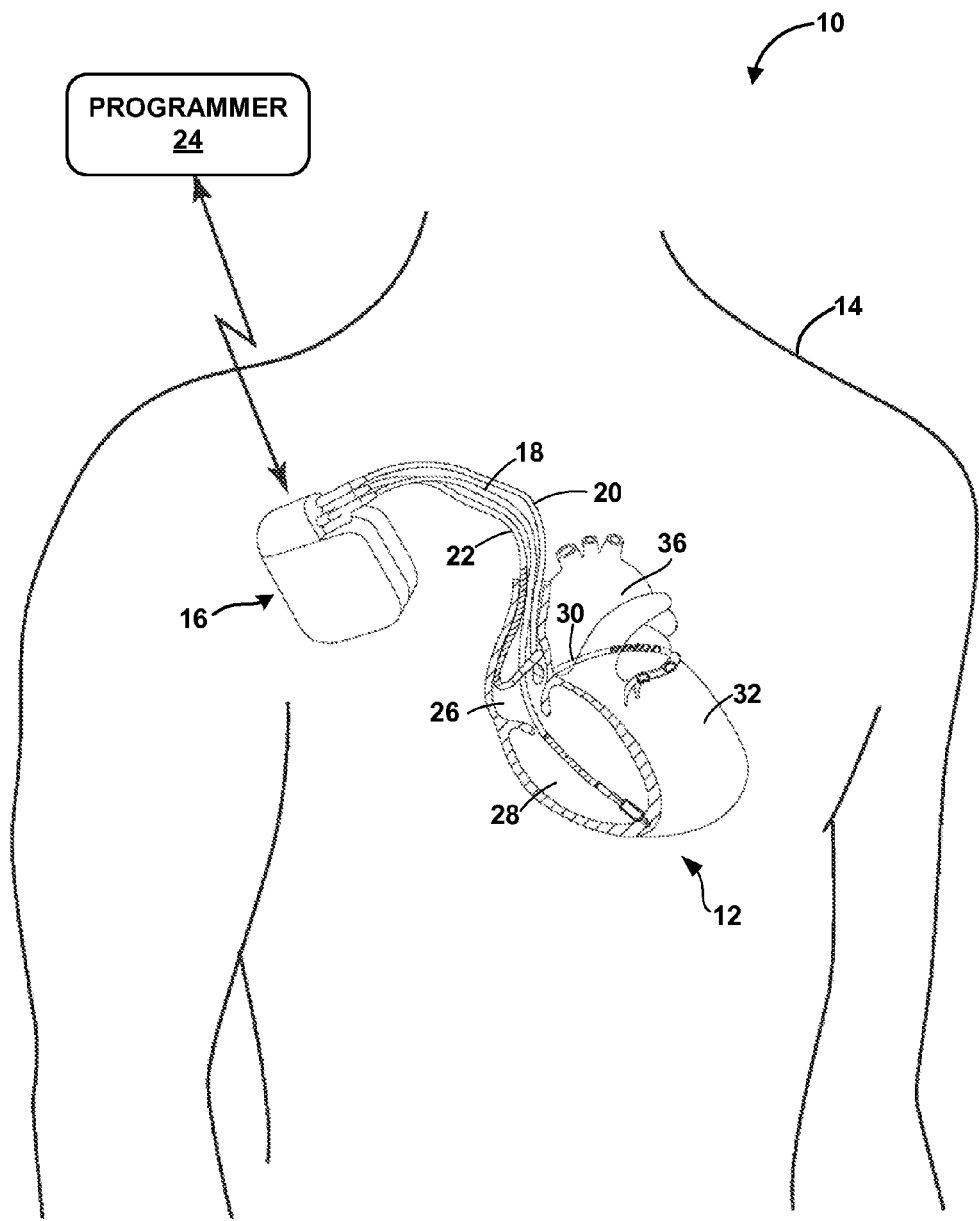
FIG. 1 is a conceptual diagram illustrating a therapy system comprising an implantable medical device (IMD) in the form of an implantable cardioverter defibrillator (ICD) for delivering stimulation therapy to a heart of a patient via implantable leads.

In general, the disclosure is directed to techniques for identification and remediation of oversensed cardiac events using far-field electrograms (FFEGMs). Lead-related conditions (e.g. fracture, insulation breach, loose set screw, or the like), EMI, myopotentials, or other noise sources may produce noise that causes oversensing of cardiac events, i.e., false detection of cardiac events. Oversensing of cardiac events due to noise can affect the operation of an IMD such as an implantable cardioverter defibrillator (ICD).

An oversensed event may refer, generally, to any cardiac event that is falsely detected due to any of a variety of factors, such as the noise sources described above. The oversensed event does not generally represent an actual physiological event within the heart, such as a ventricular depolarization (R wave), but instead an artifact of a noise source, such as a fractured conductor in a lead or some other lead-related condition. In contrast, a valid, detected cardiac event will be based on signal characteristics consistent with an actual physiological activity of the heart.

Oversensing may cause an implantable cardioverter defibrillator (ICD) or other IMD to deliver inappropriate cardioversion or defibrillation shocks. In particular, oversensing may result in an erroneous indication of arrhythmia, causing the ICD to deliver an unnecessary shock. Unnecessary shocks can be painful, potentially pro-arrhythmic, and consume excessive amounts of power from finite battery resources.

In addition, in an ICD, oversensing may cause syncope and asystole in pacemaker-dependent patients. Increased numbers of pacemaker-dependent patients are receiving ICDs, including Cardiac Resynchronization Therapy (CRT) devices. Oversensing may cause bradycardia pacing to be inhibited due to an erroneous indication of arrhythmia. For example, during a detected arrhythmia, the ICD may inhibit pacing to avoid affecting detection of ventricular fibrillation, or to avoid the possibility of pacing the patient into ventricular fibrillation.

Also, if the noise source is a fractured lead, in addition to causing oversensing, there may be an added risk of failure to capture the heart with a pacing pulse due to a compromised conductor. In this case, even if pacing is not inhibited, syncope and asystole may still be a concern if the same conductor used to sense cardiac events is also used to deliver cardioversion, defibrillation or pacing therapy to the patient.

Noise may cause oversensing on individual sensing vectors or multiple sensing vectors. A sensing vector generally refers to an electrode configuration comprising a combination of electrodes used to sense a cardiac signal. Lead-related conditions may cause oversensing on a single lead or on limited set of sensing vectors. Fracture of a conductor within a lead may cause oversensing on a particular sensing vector comprising a particular combination of electrodes associated with the lead. However, the oversensing may not affect other sensing vectors that do not rely on electrodes coupled to the fractured conductor.

In accordance with some aspects of this disclosure, an ICD may use different sensing vectors comprising different electrode configurations to identify oversensing on another sensing vector. For example, a far-field electrogram (FFEGM) may be used to identify oversensing in a near-field electrogram (NFEGM). A NFEGM may refer, for example, to an electrogram obtained via a particular, near-field set of electrodes carried by one or more leads. An FFEGM may refer to an electrogram obtained via a different, far-field set of electrodes carried by the same lead or different leads.

The far-field set of electrodes may be positioned at some distance from the near-field set of electrodes, e.g., using one or more electrodes on the same lead as the electrodes used to obtain the NFEGM, on a different lead than the electrodes used to obtain the NFEGM, within the same chamber as the electrodes used to obtain the NFEGM, or within a different chamber than the electrodes used to obtain the NFEGM.

If the primary sensing electrode configuration used to obtain the NFEGM is formed by a tip electrode and ring electrode on a right ventricular lead, for example, the FFEGM electrode sensing configuration may include electrodes in any of a wide variety positions, including without limitation other electrodes on right ventricular lead, electrodes on a left ventricular lead, electrodes on an atrial lead, including various bipolar and unipolar combinations.

In some cases, the sensing electrode configurations used to obtain the FFEGM signal may advantageously include electrodes that are coupled to different lead conductors than the electrodes used to obtain the NFEGM signal, thereby bypassing potential lead faults that may cause oversensed events in the NFEGM signal. In other cases, the sensing electrode configurations used to obtain the FFEGM signal may share one electrode in common with the sensing electrode configuration used to obtain the NFEGM signal.

One example of a NFEGM is a right ventricular NFEGM obtained via a tip electrode and ring electrode of an implantable cardioverter defibrillator (ICD) lead implanted within a patient. For this NFEGM, one example of a FFEGM with respect to the near-field tip-ring electrode configuration is a FFEGM obtained via a coil electrode on an ICD lead implanted within the patient and a can electrode carried on an ICD housing implanted within the patient. The tip and ring electrodes may be designed to deliver cardiac pacing therapy to the right ventricle of the patient's heart. The coil electrode and can electrode may be designed to deliver defibrillation energy to the right ventricle of the patient's heart. A variety of other electrode configurations may be used to obtain NFEGMs and FFEGMs.

When oversensing is identified, indicating false detection of an arrhythmia, an ICD may trigger delivery of pacing. In accordance with some aspects of this disclosure, the ICD may deliver multiple pacing pulses in short succession. For example, the ICD may deliver first pacing therapy via a first stimulation electrode configuration, and deliver second pacing therapy via a second stimulation electrode configuration. In this manner, the ICD may pace from multiple pacing vectors to provide redundancy in the event the oversensing is caused by a fractured conductor in one of the pacing vectors.

In addition to multi-vector pacing, the ICD may measure lead impedance during, before or following delivery of the pacing pulses to confirm that the lead conductors are intact. If the impedance check indicates a potential lead fracture, the ICD may select a different pacing vector. Delivery of pacing via multiple vectors and impedance-based vector selection may be programmable or automatic features of the ICD. For example, these features may be automatically activated if the ICD patient is pacemaker-dependent, e.g., based on recent or frequent delivery of pacing to the patient.

In other aspects, the ICD may identify detected cardiac events in the NFEGM signal as oversensed events based on one or more characteristics of the FFEGM signal at a time substantially coincident with the respective detected cardiac event. Examples of FFEGM signal characteristics may include an amplitude, slope, variability or other characteristic of the FFEGM signal relative within a timing window substantially coincident with the respective detected cardiac event.

The FFEGM signal is obtained from an electrode sensing configuration that is different from the primary sensing electrode configuration and may provide a signal that is generally unaffected by oversensing in the NFEGM signal. For example, the FFEGM signal may be acquired using a sense electrode configuration that does not involve a source of noise, such as a fractured conductor. Consequently, the FFEGM signal can be used for cross-correlation to determine whether a detected cardiac event is an oversensed event. Once a detected cardiac event is identified as an oversensed event, the ICD may apply a remediation technique to reduce the likelihood of unnecessary shocks or inhibited pacing.

As an example, for remediation, the ICD may adjust an R-R interval tracked for purposes of triggering cardioversion, defibrillation or pacing. The detected cardiac events may be R-waves detected in the NFEGM. The R-R interval indicates the time between successive detected R waves, i.e., successive detected ventricular depolarizations of the heart. Numerous short R-R intervals or varied R-R intervals may indicate the presence of an arrhythmia. Numerous oversensed events may result in numerous short or varied R-R intervals. The ICD may maintain a ventricular fibrillation (VF) count that is calculated at least in part as a function of the number of short R-R intervals (i.e., R-R intervals less than a threshold time period in length) in a given period of time.

When the VF count exceeds a threshold level, the ICD delivers cardioversion or defibrillation. When oversensing causes numerous short R-R intervals, however, the ICD may deliver an inappropriate shock. If R-R intervals are too long, the ICD ordinarily triggers delivery of a bradycardia pacing pulse according to a lower rate interval threshold, thereby providing low rate, backup pacing. When oversensed events produce short R-R intervals, however, there may be no opportunity to reach an R-R interval that triggers pacing. Hence, oversensed events may result in inappropriate shocks as well as inappropriately inhibited pacing. Inhibited pacing in the case of oversensing may result in syncope and asystole.

According to an example remediation technique, an ICD may use identification of oversensed events to keep the VF counter from reaching the number of intervals for detection (NID) threshold, and to reduce the number of short intervals due to oversensing. If the VF counter increments, but does not reach the NID, then a detection and resulting shock is withheld. By eliminating R-R intervals that are caused by oversensed events, the number of erroneous short R-R intervals can be reduced, thereby preventing the VF counter from reaching the NID threshold, and avoiding an unnecessary and inappropriate cardioversion or defibrillation shock.

Eliminating short R-R intervals caused by oversensed events also may have the effect of lengthening R-R intervals to trigger pacing. In particular, the ICD may sum the R-R interval caused by an oversensed event with the R-R interval generated by the next detected cardiac event (e.g., detected R wave) that has not been identified as an oversensed event. This summation of erroneous short intervals will lengthen the R-R intervals, reducing the number of R-R intervals that increment the VF counter. In addition, the R-R intervals will accumulate to produce an overall R-R interval that reaches the length of the lower rate interval that triggers pacing. As one example, the lower rate interval could be approximately two seconds, which corresponds to a pulse rate of thirty beats per minute, and may be sufficient to avoid syncope and asystole. In this manner, the ICD can provide low rate, backup pacing during lead noise, and especially during lead failure.

According to another example remediation technique, an ICD may trigger pacing if at least a minimum number of oversensed R wave events are identified in a given period. For example, in a dual chamber ICD, having atrial and ventricular leads, the ICD may trigger pacing if at least a minimum number of oversensed R wave events are identified since a previous detected atrial event, i.e., a detected P wave, atrial pace or atrial refractory event. The ICD may deliver a pacing pulse after the next detected atrial event, e.g., at a programmed atrial-ventricular (AV) pacing interval (e.g., 250 milliseconds (ms) after the detected atrial event).

In some cases, two or more pacing pulses may be delivered as multiple, short coupled pacing pulses in quick succession, e.g., where a second pulses if deliver 5 to 100 milliseconds (ms) after the initial pacing pulse, using different stimulation vectors (e.g., bipolar, unipolar, left ventricular). During, before or after delivery of each pacing pulse, impedance can be monitored to evaluate the integrity of the stimulation path. Impedance monitoring can be programmed or automatically activated for pacemaker dependent patients, e.g., patients with more than 50% paced beats.

For a single-chamber ICD, i.e., having only a right ventricular lead, the ICD may trigger pacing if at least a minimum number of oversensed R wave events are identified in a specified period of time. The period of time may be, for example, a period of time following a previous non-oversensed R wave event. At the end of the period of time, the ICD may deliver a pacing pulse. Again, the ICD may, in some cases, deliver two or more pacing pulses in quick succession e.g., 5 to 100 milliseconds (ms) apart, using different stimulation vectors, and monitor impedance during each pacing pulse to evaluate the integrity of the stimulation path. In either case, dual or single chamber, the ICD reduces the likelihood that pacing may be inhibited due to oversensed events, and reduces the risk of syncope and asystole as a result of inhibited pacing.

FIG. 1 is a conceptual diagram illustrating an example therapy system 10 that may be used to provide therapy to heart 12 of patient 14. Therapy system 10 includes ICD 16, which is coupled to leads 18, 20, and 22, and programmer 24. ICD 16 may be, for example, a combined implantable pacemaker, cardioverter, defibrillator that provides electrical signals to heart 12 via electrodes coupled to one or more of leads 18, 20, and 22. ICD 16 may be configured to implement various techniques for identification and remediation of oversensed events using FFEGM signals, as described in this disclosure.

Although the oversensing identification and remediation techniques are described with respect to an ICD with support for pacing, cardioversion and defibrillation therapies, they may be implemented in other types of IMDs, such as ICDs without support for pacing therapy or in pacemakers without support for cardioversion or defibrillation therapy. Accordingly, ICD 16 is described for purposes of illustration, and without limitation of the techniques as broadly described in this disclosure.

With further reference to FIG. 1, leads 18, 20, 22 extend into the heart 12 of patient 14 to sense electrical activity of heart 12 and/or deliver electrical stimulation to heart 12. Patient 12 is ordinarily, but not necessarily, a human patient. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into right atrium 26 of heart 12.

In some alternative embodiments, therapy system 10 may include an additional lead or lead segment (not shown in FIG. 1) that deploys one or more electrodes within the vena cava or other vein. These electrodes may allow alternative electrical sensing configurations to provide improved sensing accuracy in some patients. Accordingly, the lead and electrode configuration of FIG. 1 is provided for purposes of illustration and without limitation.

ICD 16 may sense electrical signals attendant to the depolarization and repolarization of heart 12 via electrodes (not shown in FIG. 1) coupled to at least one of the leads 18, 20, 22. In some examples, ICD 16 provides pacing pulses to heart 12 based on the electrical signals sensed within heart 12. The configurations of electrodes used by ICD 16 for sensing and pacing may be unipolar or bipolar.

ICD 16 also provides defibrillation therapy and/or cardioversion therapy via electrodes located on at least one of the leads 18, 20, 22. ICD 16 may detect arrhythmia of heart 12, such as fibrillation of ventricles 28 and/or 32, and deliver cardioversion or defibrillation therapy to heart 12 in the form of electrical shocks. In some examples, ICD 16 may be programmed to deliver a progression of therapies, e.g., pulses with increasing energy levels, until a tachyarrhythmia of heart 12 is stopped. ICD 16 may detect tachycardia or fibrillation employing one or more detection techniques known in the art.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions.

Programmer 24 can additionally or alternatively include a peripheral pointing device, such as a mouse, via which a user may interact with the user interface. In some aspects, a display of programmer 24 may include a touch screen display, and a user may interact with programmer 24 via the display. It should be noted that the user may also interact with programmer 24 or ICD 16 remotely via a networked computing device.

A user, such as a physician, technician, surgeon, electrophysiologist, or other clinician, may interact with programmer 24 to communicate with ICD 16. For example, the user may interact with programmer 24 to retrieve physiological or diagnostic information from ICD 16. A user may also interact with programmer 24 to program ICD 16, e.g., select values for operational parameters of ICD 16.

For example, the user may use programmer 24 to retrieve information from ICD 16 regarding the rhythm of heart 12, trends therein over time, or arrhythmic episodes. As another example, the user may use programmer 24 to retrieve information from ICD 16 regarding other sensed physiological parameters of patient 14, such as intracardiac or intravascular pressure, activity, posture, respiration, or thoracic impedance. As another example, the user may use programmer 24 to retrieve information from ICD 16 regarding the performance or integrity of ICD 16 or other components of system 10, such as leads 18, 20 and 22, or a power source of ICD 16.

The user may use programmer 24 to program a therapy progression, select electrodes used to deliver pacing and defibrillation pulses, select waveforms for the pacing and defibrillation pulses, or select or configure the fibrillation detection algorithm for ICD 16. As described in this disclosure, the fibrillation detection algorithm may employ techniques for identification and remediation of oversensed events, e.g., to avoid delivery of inappropriate shocks and to avoid inappropriate inhibition of pacing pulses, particularly due to oversensing caused by lead fracture noise.

Pacemaker dependent patients may not be paced during lead failure noise or may not capture the heart due to fractured conductors. With techniques for identification and remediation of oversensed events, in some cases, ICD 16 can deliver bradycardia pacing during ICD lead failure noise. Pacing can be timed to avoid pacing during a T wave or during actual ventricular fibrillation.

The user may also use programmer 24 to program similar aspects of other therapies provided by ICD 16, such as cardioversion or pacing therapies. In some examples, the user may activate certain features of ICD 16 by entering a single command via programmer 24, such as depression of a single key or combination of keys of a keypad or a single point-and-select action with a pointing device.

ICD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the ICD 16 implant site in order to improve the quality or security of communication between ICD 16 and programmer 24.

ICD 16 is an example of a device that may acquire, store and analyze near-field electrograms (NFEGMs) and far-field electrograms (FFEGMs). In particular, ICD 16 may detect cardiac events such as R waves in an NFEGM and identify whether the detected cardiac events are oversensed events based on one or more characteristics of an FFEGM. Such EGMs may be processed by ICD 16 to support identification and remediation of oversensed events.

ICD 16 may produce interval data indicating intervals between detection of various detected cardiac events. The detected cardiac events and interval data may be recorded in marker channel data along with cardiac events induced by the ICD, i.e., by delivery of pacing pulses, cardioversion shocks, or defibrillation shocks. The detected cardiac events define intervals that may be used by ICD 16 to control delivery of pacing, cardioversion, and/or defibrillation therapies to patient 12.

EGMs may be retrieved from ICD 16 by programmer 24, and displayed by programmer 24 for evaluation by a clinician or other user to, for example, determine whether a sensing integrity condition is present in ICD 16, leads 18, 20 and 22, or any other components of system 10. The EGMs may be considered in conjunction within other data, such as lead impedance data, which may also be stored by ICD 16, and retrieved and displayed by programmer 24.

Figure 2:
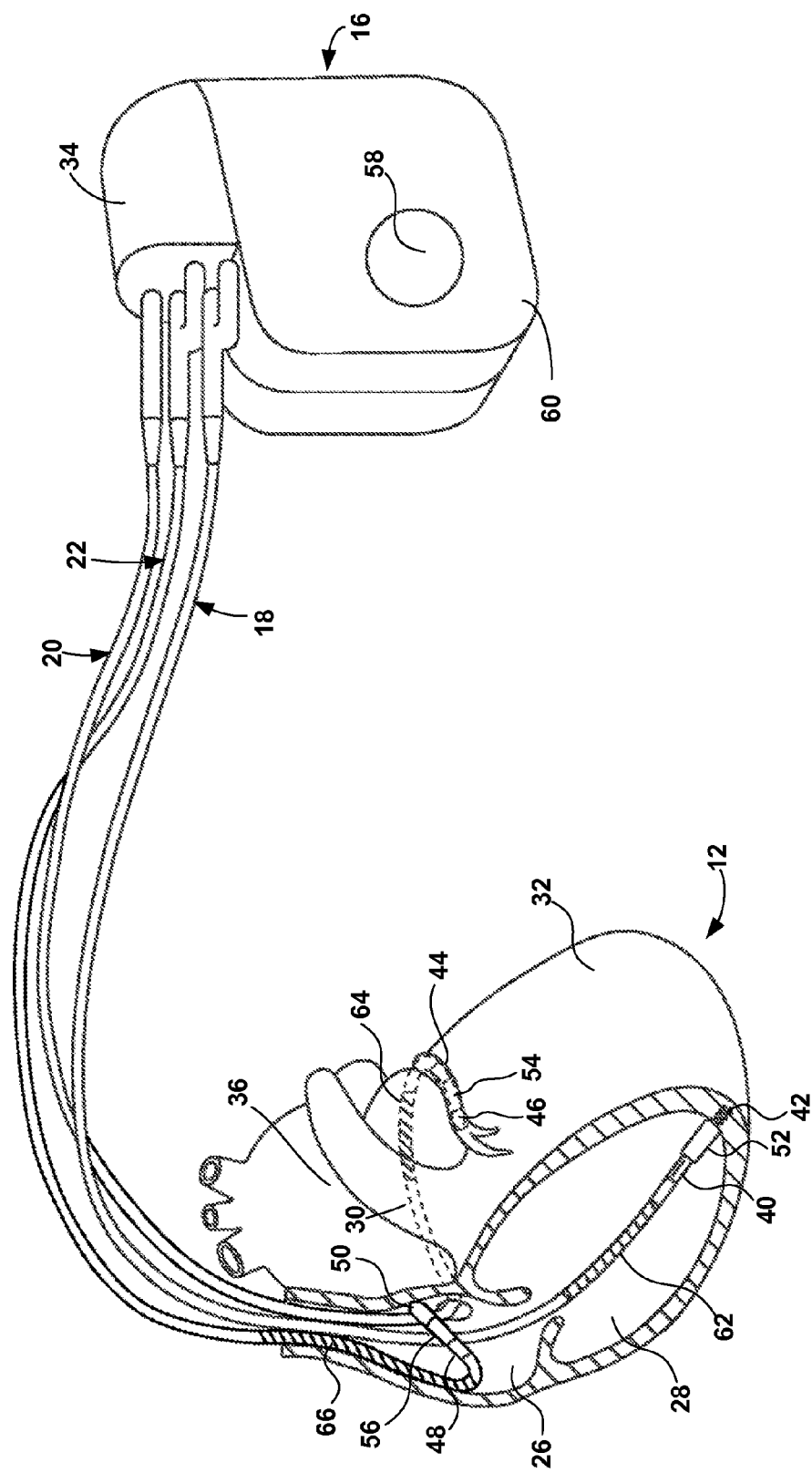
FIG. 2 is a conceptual diagram further illustrating the ICD and leads of the system of FIG. 1 in conjunction with the heart.

FIG. 2 is a conceptual diagram illustrating a three-lead ICD 16 and leads 18, 20 and 22 of therapy system 10 in greater detail. Leads 18, 20, 22 may be electrically coupled to a stimulation module and a sensing module of ICD 16 via connector block 34. In some examples, proximal ends of leads 18, 20, 22 may include electrical contacts that electrically couple to respective electrical contacts within connector block 34 of ICD 16. Also, in some examples, leads 18, 20, 22 may be mechanically coupled to connector block 34 with the aid of set screws, connection pins, snap connectors, or other suitable mechanical coupling mechanisms.

Each of leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36 in the illustrated example of FIG. 2, but electrodes may be provided in left atrium 36 in alternative implementations.

Electrodes 40, 44, and 48 may take the form of ring electrodes, and electrodes 42, 46, and 50 may take the form of extendable helix tip electrodes mounted within insulative electrode heads 52, 54, and 56, respectively. In other embodiments, one or more of electrodes 42, 46, and 50 may take the form of small circular electrodes at the tip of a lead tine or other fixation element. Leads 18, 20, 22 also include elongated electrodes 62, 64, 66, respectively, which may take the form of an elongated coil that may be used to deliver cardioversion and/or defibrillation shocks. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 2, ICD 16 includes one or more housing electrodes, such as housing electrode 58, which may be formed integrally with an outer surface of hermetically-sealed housing 60 of ICD 16 or otherwise coupled to housing 60. In some examples, housing electrode 58 is defined by an uninsulated portion of an outward facing portion of housing 60 of ICD 16. Other divisions between insulated and uninsulated portions of housing 60 may be employed to define two or more housing electrodes. In some examples, housing electrode 58 comprises substantially all of housing 60. As described in further detail with reference to FIG. 4, housing 60 may enclose an electrical stimulation module that generates therapeutic stimulation, such as cardiac pacing pulses and cardioversion or defibrillation shocks, as well as an electrical sensing module for monitoring the rhythm of heart 12.

ICD 16 may sense electrical cardiac signals in the form of EGMs attendant to the depolarization and repolarization of heart 12 via electrodes 40, 42, 44, 46, 48, 50, 58, 62, 64, and 66. The electrical cardiac signals are conducted to ICD 16 from the electrodes via the respective leads 18, 20, 22 or, in the case of housing electrode 58, a conductor coupled to housing electrode 58. ICD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

Any multipolar combination of two or more of electrodes 40, 42, 44, 46, 48, 50, 58, 62, 64, and 66 may be considered a sensing electrode configuration forming a sensing vector. One example of a sensing vector formed by a sensing electrode configuration comprising a bipolar electrode combination on the same lead, such as the combination formed by tip electrode 42 and ring electrode 40 of lead 18. On one lead having three electrodes, there may be at least three different sensing electrode configurations available to ICD 16. For lead 18, these bipolar sensing electrode configurations are tip electrode 42 and ring electrode 40, tip electrode 42 and elongated coil electrode 62, and ring electrode 40 and elongated coil electrode 62.

In some cases, sense electrode configurations having electrodes on two different leads may be used. Further, as mentioned above, a sensing electrode configuration may utilize housing electrode 58, which may provide a unipolar sensing electrode configuration in combination with any of the electrodes on the lead. As an example, elongated coil electrode 62 and housing electrode 58 may provide a unipolar, coil-can sensing electrode configuration. In some examples, a sensing electrode configuration may comprise multiple housing electrodes 58. In any sensing electrode configuration, the polarity of each electrode may be configured as appropriate for the application of the sensing electrode configuration.

ICD 16 may deliver electrical stimulation therapy, such as pacing pulses or cardioversion or defibrillation shocks, via various stimulation vectors comprising different stimulation electrode configurations. In some examples, ICD 16 delivers pacing pulses via bipolar combinations of electrodes 40, 42, 44, 46, 48 and 50 to produce depolarization of cardiac tissue of heart 12. In other examples, ICD 16 delivers pacing pulses via any of electrodes 40, 42, 44, 46, 48 and 50 in combination with housing electrode 58 in a unipolar configuration.

Furthermore, ICD 16 may deliver defibrillation shocks to heart 12 via any combination of elongated coil electrodes 62, 64, 66 and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, ICD 16 need not be implanted within patient 14. In examples in which ICD 16 is not fully implanted in patient 14, ICD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to ICD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from ICD 16 into right atrium 26 or right ventricle 28, or two leads that extend into a respective one of the right ventricle 26 and right atrium 26. An example of this type of therapy system is shown in FIG. 3.

Figure 3:
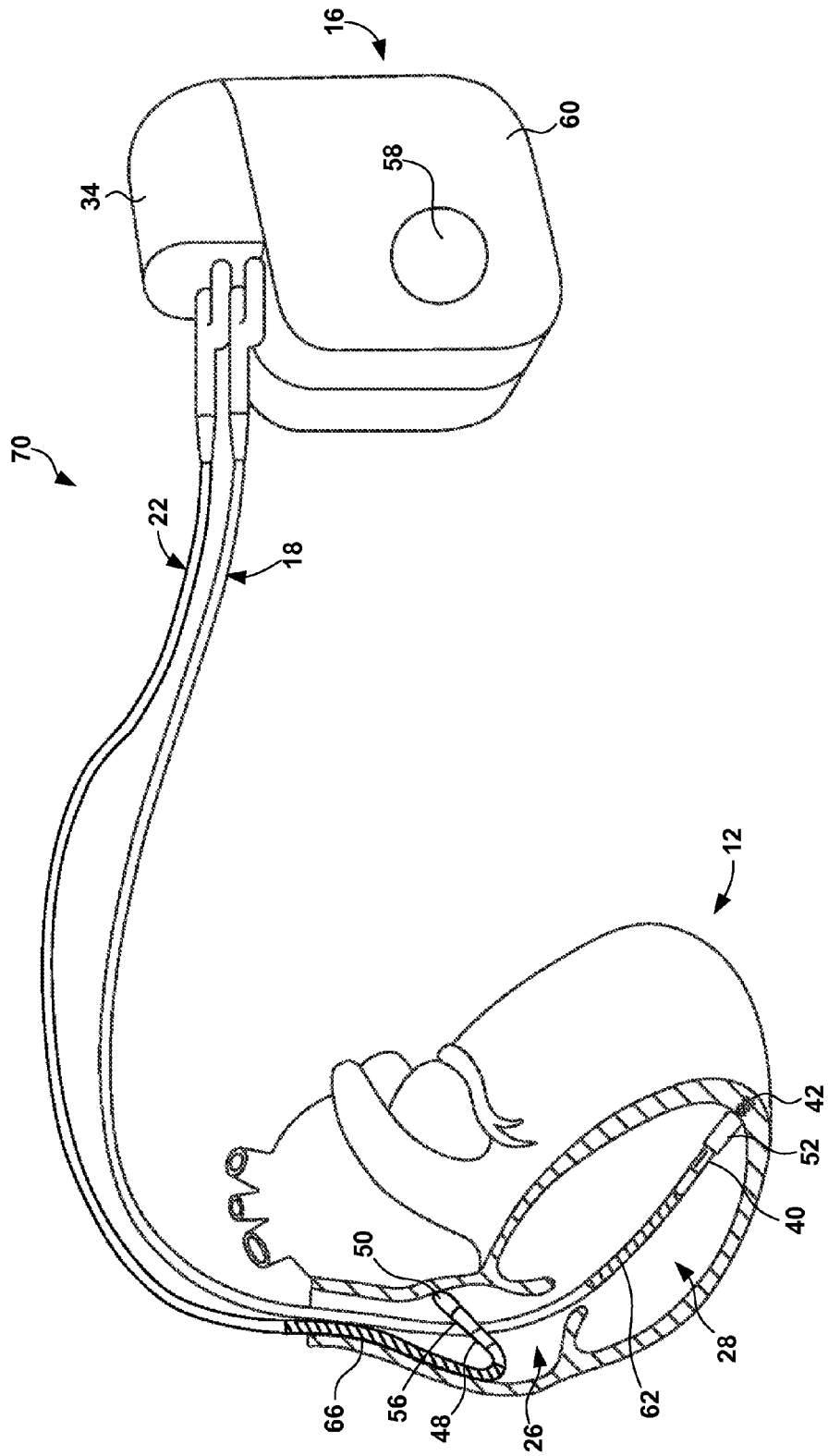
FIG. 3 is a conceptual diagram illustrating another example therapy system comprising the ICD of FIG. 1 coupled to a different configuration of leads.

FIG. 3 is a conceptual diagram illustrating another example of therapy system 70, which is similar to therapy system 10 of FIGS. 1 and 2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12. Storage of EGMs according to the techniques described herein may also be performed by or with respect to system 70.

Figure 4:
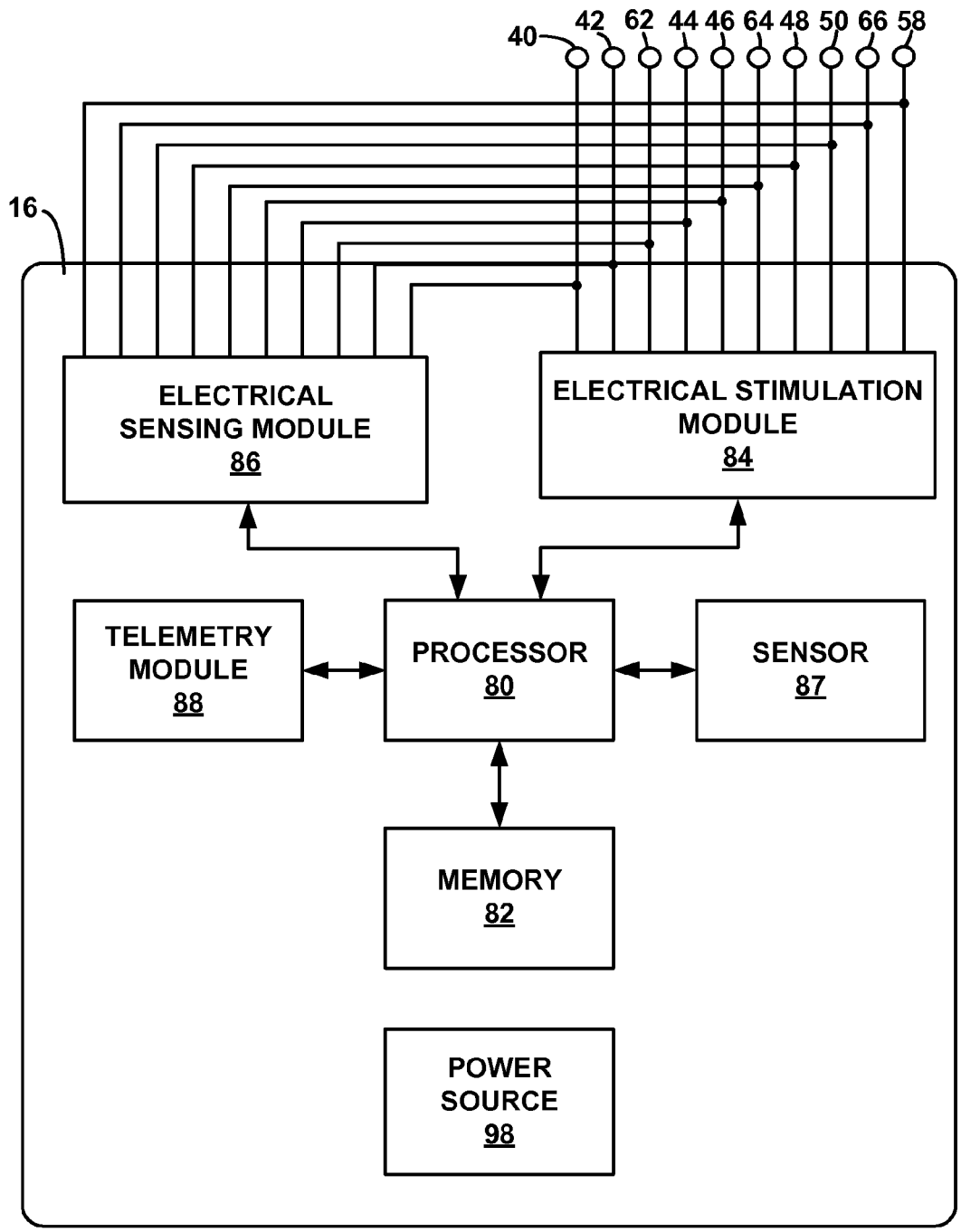
FIG. 4 is a functional block diagram illustrating example components of the ICD of FIG. 1.

FIG. 4 is a functional block diagram illustrating one example configuration of ICD 16. In the example illustrated by FIG. 4, ICD 16 includes a processor 80, memory 82, electrical stimulation module 84, electrical sensing module 86, sensor 87, telemetry module 88, and power source 98. Memory 82 may includes computer-readable instructions that, when executed by processor 80, cause ICD 16 and processor 80 to perform various functions attributed to ICD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The various components of ICD 16 are coupled to power source 98, which may include a rechargeable or non-rechargeable battery. A non-rechargeable battery may be capable of holding a charge for several years, while a rechargeable battery may be inductively charged from an external device, e.g., on a daily or weekly basis. Power source 98 also may include power supply circuitry for providing regulated voltage and/or current levels to power the components of ICD 16.

Processor 80 may include any one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

In accordance with various aspects of this disclosure, ICD 16 may be configured to acquire a first cardiac signal via a first sense electrode configuration (e.g., an NFEGM signal), acquire a second cardiac signal via a second sense electrode configuration (e.g., a FFEGM signal), detect cardiac events in the first cardiac signal (e.g., R waves), identify at least some of the cardiac events detected in the first cardiac signal as oversensed events based on whether one or more characteristics (e.g., amplitude, slope, variability) of the second cardiac signal confirm the cardiac events, and control delivery of cardiac electrical stimulation therapy to a patient based on the identification of the oversensed events.

In some examples, ICD 16 may determine time intervals between the detected events that are not identified as oversensed events, and control delivery of electrical stimulation therapy to the patient based on the time intervals. In particular, ICD 16 may detect that one of the time intervals is greater than a threshold time interval, and deliver pacing therapy to the patient in response to the detection that one of the time intervals is greater than the threshold time interval. The pacing therapy may include first pacing therapy delivered via a first stimulation electrode configuration and second pacing therapy delivered via a second stimulation electrode configuration. The first and second stimulation electrode configurations may be formed by electrodes on the same lead or different leads, and may be positioned to deliver pacing to the same chamber or different chambers of the heart.

In some examples, ICD 16 may determine a count of a number of the time intervals that are shorter than a threshold time interval, detect that the count is greater than a threshold count, and deliver at least one of cardioversion or defibrillation therapy to the patient in response to the detection that the count is greater than the threshold count. In other examples, ICD 16 may detect that one of the time intervals is greater than a threshold time interval, deliver pacing therapy to the patient in response to the detection that one of the time intervals is greater than the threshold time interval, determine a count of a number of the time intervals that are shorter than a threshold time interval, detect that the count is greater than a threshold count, and deliver at least one of cardioversion or defibrillation therapy to the patient in response to the detection that the count is greater than the threshold count.

With further reference to FIG. 4, processor 80 controls electrical stimulation module 84 to deliver stimulation therapy to heart 12. Processor 80 may control electrical stimulation module 84 to deliver stimulation according to a selected one or more therapy programs, which may be stored in memory 82. For example, processor 80 may control electrical stimulation module 84 to deliver electrical pacing pulses or cardioversion or defibrillation shocks with the amplitudes, pulse widths, frequencies, or electrode polarities specified by the selected therapy programs.

Electrical stimulation module 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of ICD 16. Electrical stimulation module 84 is configured to generate and deliver electrical stimulation therapy to heart 12. For example, electrical stimulation module 84 may deliver defibrillation shocks to heart 12 via at least two electrodes 58, 62, 64, 66.

Electrical stimulation module 84 may deliver pacing pulses via ring electrodes 40, 44, 48 coupled to leads 18, 20, and 22, respectively, and/or helical tip electrodes 42, 46, and 50 of leads 18, 20, and 22, respectively. In some examples, electrical stimulation module 84 delivers pacing, cardioversion, or defibrillation stimulation in the form of electrical pulses or shocks. In other examples, electrical stimulation module 84 may deliver one or more of these types of stimulation in the form of other signals, such as sine waves, square waves, or other substantially continuous signals.

Electrical stimulation module 84 may include a switch module and processor 80 may use the switch module to select, e.g., via a data/address bus, which of the available electrodes are used to deliver pacing, cardioversion, or defibrillation pulses. The switch module may include a switch array, switch matrix, multiplexer, or any other type of switching device suitable to selectively couple stimulation energy to selected electrodes.

Electrical sensing module 86 monitors signals from electrode sensing vectors formed by different electrode sensing configurations. Electrode sensing configurations are defined by various combinations of electrodes 40, 42, 44, 46, 48, 50, 58, 62, 64 or 66 in order to monitor electrical activity of heart 12. For example, electrical sensing module 86 may acquire electrical cardiac signals in the form of NFEGMs and FFEGMs. Electrical sensing module 86 may include a switch module to select which of the available electrodes are used to sense the heart activity.

In some examples, processor 80 may select the electrodes that function as sense electrodes, or the sensing electrode configuration, via the switch module within electrical sensing module 86, e.g., by providing signals via a data/address bus. Electrical sensing module 86 may include multiple detection channels, each of which may comprise an amplifier. The detection channels may be configured to detect different cardiac events, such as P waves, R waves and the like. In response to the signals from processor 80, the switch module within electrical sensing module 86 may couple selected electrodes to each of the detection channels to acquire a desired EGM for detection of cardiac events.

If ICD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other components of processor 80, such as a microprocessor, or a software module executed by a component of processor 80, which may be a microprocessor or ASIC.

The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals to electrical sensing module 86 to blank one or more channels, e.g., amplifiers, for a period during and after delivery of electrical stimulation to heart 12. The durations of these intervals may be determined by processor 80 in response to stored program data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves with detection channels of electrical sensing module 86. Noise may produce oversensing of R-wave events that cause the ventricular escape interval counter to reset. The oversensed R-waves produced by one or more of the detection channels produce short R-R intervals that may inhibit delivery of pacing pulses. Techniques for identification and remediation of oversensed cardiac events, as described in this disclosure, may prevent inhibition of pacing due to oversensing caused by noise. Electrical stimulation module 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by electrical stimulation module 84, and thereby control the basic timing of cardiac pacing functions, including anti-tachyarrhythmia pacing.

The value of the count present in the escape interval counters when reset by sensed R-waves and P-waves may be used by processor 80 to detect cardiac events and measure the durations of R-R intervals, P-P intervals, P-R intervals and R-P intervals, which are measurements that may be stored in memory 82. Processor 80 may use the count in the interval counters to detect a tachyarrhythmia event, such as an atrial or ventricular fibrillation or tachycardia. The R-R intervals indicated by the count, in particular, may be used to increment a VF counter to control delivery of cardioversion or defibrillation shocks. The VF counter may form part of a cardioversion/defibrillation control module implemented by processor 80. Again, the VF counter may be incremented in response to detection of short R-R intervals, and possibly in response to other events such as R-R interval variance. The VF counter triggers delivery of a defibrillation shock when the counter reaches the NID threshold.

In some examples, processor 80 may operate as an interrupt-driven device that is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998, or in U.S. patent application Ser. No. 10/755,185, filed Jan. 8, 2004 by Kevin T. Ousdigian, entitled "REDUCING INAPPROPRIATE DELIVERY OF THERAPY FOR SUSPECTED NON-LETHAL ARRHYTHMIAS." U.S. Pat. No. 5,545,186 to Olson et al., U.S. Pat. No. 5,755,736 to Gillberg et al., and U.S. patent application Ser. No. 10/755,185 by Kevin T. Ousdigian are incorporated herein by reference in their entireties. However, other arrhythmia detection methodologies may also be employed by processor 80 in other examples.

In the event that processor 80 detects an atrial or ventricular tachyarrhythmia based on signals from electrical sensing module 86, and an anti-tachyarrhythmia pacing regimen is desired, timing intervals for controlling the generation of anti-tachyarrhythmia pacing therapies by electrical stimulation module 84 may be loaded by processor 80 into the pacer timing and control module to control the operation of the escape interval counters therein and to define refractory periods during which detection of R-waves and P-waves is ineffective to restart the escape interval counters.

Electrical stimulation module 84 also includes a high voltage charge circuit and a high voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like the pacer timing and control module, be a hardware component of processor 80 and/or a firmware or software module executed by one or more hardware components of processor 80. The cardioversion/defibrillation control module may initiate charging of the high voltage capacitors of the high voltage charge circuit of electrical stimulation module 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion shock by electrical stimulation module 84 is controlled by the cardioversion/defibrillation control module of processor 80. Following delivery of the fibrillation or tachycardia therapy, processor 80 may return electrical stimulation module 84 to a cardiac pacing function and await the next successive interrupt due to pacing or the occurrence of a sensed atrial depolarization (P wave) or ventricular depolarization (R wave).

Electrical stimulation module 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or by a switching module of electrical stimulation module 84 of ICD 16.

ICD 16 may comprise one or more sensors, such as sensor 87 illustrated in the example of FIG. 4. Sensor 87 may be within housing 60 (FIG. 2) of ICD 16. ICD 16 may additionally or alternatively be coupled to one or more sensors located outside of housing 60 of ICD 16. Sensor 87 may be located on or within on or more of leads 18, 20 and 22, or another lead which may or may not include stimulation/sensing electrodes. In some examples, sensor 87 may be separately housed from ICD 16, and may be coupled to ICD 16 via wireless communication. Sensor 87 may be implanted or external.

Sensor 87 may comprise, as examples, a pressure sensor, a motion sensor, a heart sound sensor, or any sensor capable of generating a signal that varies a function of mechanical activity, e.g., contraction, of heart 12. A pressure sensor may be, for example, a capacitive pressure sensor that senses an intracardiac or other cardiovascular pressure. A motion sensor may be, for example, an accelerometer or piezoelectric element. Processor 80 may receive one or more signals from sensor 87 or a plurality of sensors. Processor 80 may monitor, among other things, the mechanical activity of heart 12 based on such signals.

In addition to obtaining EGMs, one or more of the sensing channels associated with electrical sensing module 86 may be configured to measure electrical impedance across various electrode configurations used for sensing or stimulation. For example, ICD 16 may monitor impedance measurements to evaluate lead integrity for sensing or stimulation. If impedance is out of range, e.g., too high or too low, processor 80 may control electrical stimulation module 84, electrical sensing module 86 or both to select different electrode configurations for use in sensing or stimulation.

Telemetry module 88 includes any suitable hardware, firmware, software or any combination thereof for communicating with another device, such as programmer 24. Under the control of processor 80, telemetry module 88 may receive downlink telemetry from and send uplink telemetry to programmer 24 with the aid of an antenna, which may be internal and/or external to ICD 16. Processor 80 may provide the data to be uplinked to programmer 24 and the control signals for the telemetry circuit within telemetry module 88, e.g., via an address/data bus.

In some examples, processor 80 may transmit atrial and ventricular cardiac signals (e.g., EGM signals) produced by atrial and ventricular sense amplifier circuits within electrical sensing module 86 to programmer 24. Programmer 24 may interrogate ICD 16 to receive the EGMs. Processor 80 may store EGMs within memory 82, and retrieve stored EGMs from memory 82. Processor 80 may also generate and store marker channel data indicative of different cardiac events detected by electrical sensing module 86, such as ventricular and atrial depolarizations, and transmit the marker channel data to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Processor 80 may store cardiac EGMs for physiological episodes, such as tachyarrhythmias, within episode logs in memory 82. For example, processor 80 may store cardiac EGMs for atrial and ventricular tachycardia and fibrillation episodes, in response to the detection of the tachycardia or fibrillation using any of the techniques described above.

In some examples according to this disclosure, processor 80 identifies cardiac events detected in NFEGMs as oversensed events based on analysis of FFEGMs. Other techniques for identifying oversensed events may be used in conjunction with the FFEGM-based techniques described in this disclosure. In some examples, processor 80 additionally or alternatively identifies an oversensed vent based on a morphological analysis of signals received from electrical sensing module 86, which may distinguish between noise and cardiac depolarizations. For example, a morphological analysis may include any one or more of an amplitude regularity analysis, an analysis of the width of the QRS complex or other features of the EGM, or an analysis of slew rates.

In some examples, a morphological analysis may involve a wavelet analysis, such as those described in U.S. Pat. No. 6,393,316, entitled "METHOD AND APPARATUS FOR DETECTION AND TREATMENT OF CARDIAC ARRHTHMIAS," which issued to Gillberg et al. on May 21, 2002, and U.S. Pat. No. 7,167,747, entitled "IDENTIFICATION OF OVERSENSING USING SINUS R-WAVE TEMPLATE," which issued to Gunderson et al. on Jan. 23, 2007. In some examples, the analysis may include the far-field EGM analysis techniques described in U.S. Pat. No. 7,333,855 to Gunderson et al., entitled "METHOD AND APPARATUS FOR DETERMINING OVERSENSING IN A MEDICAL DEVICE," which issued on Feb. 19, 2008. The entire content of each of U.S. Pat. Nos. 6,393,316, 7,167,747 and 7,333,855 is incorporated herein by reference in its entirety.

As described in this disclosure, techniques for identification and remediation of oversensed events make identify oversensed events detected in a NFEGM based on analysis of a FFEGM. The NFEGM and FFEGM may be obtained via different sensing channels of electrical sensing module 86. The NFEGM may be obtained via a sensing channel coupled to a primary sensing electrode configuration. The FFEGM may be obtained via a different sensing channel coupled to a sensing electrode configuration different from the primary sensing electrode configuration. Different sensing channels may include a different sensing electrode configurations used by electrical sensing module 86 to detect a cardiac signal and/or different signal processing circuitry, e.g., a different channel or amplifier, of electrical sensing module 86.

As another feature, processor 80 may detect mechanical activity (e.g., contraction) of heart 12 based on the signals provided by one or more sensors 87. In this case, processor 80 may determine whether cardiac events detected by electrical sensing module 86 in the NFEGM are correlated with mechanical activity of the heart to determine whether the cardiac event represents physiological activity of the heart 12 or oversensing resulting from noise, such as lead noise caused by lead fracture.

A pacer timing and control module and cardioversion/defibrillation control module, each of which may be implemented as a hardware component of processor 80 and/or a firmware or software module executed by one or more hardware components of processor 80, may operate to deliver pacing and cardioversion or defibrillation shocks based at least in part on cardiac events such as R waves detected in a cardiac signal by electrical sensing module 86. As discussed above, the cardiac signal may be a NFEGM produced by a primary sensing electrode configuration, such as a combination of a tip electrode 42 and a ring electrode 40 on a right ventricular lead 18. Again, the NFEGM may be susceptible to noise sources such as lead noise that cause oversensing, i.e., erroneous sensing of cardiac events such as R waves.

In general, a pacer timing and control module and cardioversion/defibrillation module may rely on R-R intervals tracked by escape interval counters. The escape interval counters are responsive to reset their counts when electrical sensing module 86 detects and indicates a pertinent event. For a counter that tracks R waves, for example, the count at the time the counter is reset in response to the next detected R wave represents the R-R interval. As explained above, oversensed events can inappropriately reset the counter, producing short or varied R-R intervals that may be interpreted as arrhythmias. The result may be inappropriate shocks and inappropriately inhibited pacing.

As described in this disclosure, processor 80 may be configured to analyze FFEGM data obtained from a sensing channel to identify whether detected cardiac events obtained from another sensing channel, e.g., a channel that senses an NFEGM signal, are oversensed events. For example, processor 80 may analyze one or more characteristics of the FFEGM signal at a time substantially coincident with a detected cardiac event. Processor 80 may compare the characteristics of the FFEGM signal to one or more criteria to determine whether such FFEGM characteristics are indicative of an actual cardiac event, such as an R wave. If not, processor 80 may conclude that the detected cardiac event is an erroneous, oversensed event. In this manner, processor 80 determines whether there is a correlation between the FFEGM signal and the detected cardiac event. In this example, processor 80 makes an oversensing determination for each individual, detected cardiac event, instead of over a series or sequence of events. If the detected cardiac event is an oversensed event, the R-R interval produced by the oversensed event is added to the next R-R interval that is not produced by oversensing.

In various implementations, processor 80 may analyze one or more of a variety of different characteristics of the FFEGM signal. Examples include amplitude, slope, variability of other characteristics of the FFEGM signal. Other characteristics may include non-physiological FFEGM signal amplifier saturation during a detected event. The characteristic or characteristics may be evaluated within a timing window that is substantially centered at the time the cardiac event is detected in the NFEGM signal. If the cardiac event is detected in the NFEGM signal at time T1, for example, processor 80 may analyze the FFEGM signal within a timing window of T1−t1 and T1+t1, where t1 is an amount of time that is added and subtracted from T1 to generate the timing window. Processor 80 may analyze the characteristics of the FFEGM signal using digital samples of the FFEGM signal obtained during the timing window, e.g., via a wide band sense channel.

As one example, processor 80 may compare an amplitude of the FFEGM signal at a time substantially coincident with the time of the detected cardiac event to a threshold amplitude. The threshold amplitude may correspond to a very low baseline, such as an isoelectric baseline, of the FFEGM within the timing window. Often, the FFEGM may exhibit a flat isoelectric baseline during oversensing noise on the NFEGM. For each detected cardiac event, processor 80 creates the timing window around the point in the FFEGM that temporally coincides with or corresponds to the detected cardiac event.

To reduce the risk of classifying an actual ventricular fibrillation (VF) event as an oversensed event due to a small ventricular fibrillation amplitude in the FFEGM signal, the threshold amplitude may be determined based on a study of actual data. For example, actual FFEGM amplitudes from induced and spontaneous ventricular fibrillation episodes can be collected, stored and compared to the threshold used to identify an oversensed event. The threshold may be adjusted based on this comparison to better ensure that the threshold support robust identification of oversensed events. In some cases, an episode may be classified as a VF episode by the clinician. The FFEGM amplitudes associated with the episode can then be used to set the FFEGM threshold amplitude of the baseline used to identify oversensed events.

As an illustration, processor 80 may create a 200 millisecond (ms) timing window around this point in the FFEGM produced by the RV coil to can electrode configuration. Within this timing window, processor 80 determines if the FFEGM includes a flat isoelectric baseline signal that indicates oversensing or a different signal that correlates with a valid cardiac event. In particular, processor 80 may make this determination by finding the amplitude of the FFEGM. For example, processor 80 may determine the amplitude as the maximum voltage minus the minimum voltage of the FFEGM within the timing window, or as an average voltage. Then, processor 80 compares the amplitude to a fixed or varying threshold amplitude. The threshold could vary as a function of an average baseline amplitude of the FFEGM signal over a period of time. If the FFEGM amplitude is less than the threshold amplitude, processor 80 determines that the detected cardiac event should be classified as an oversensed event.

If FFEGM slope or variability are used as alternatives to or in combination with FFEGM amplitude, such characteristics may be determined by processor 80 using a variety of computational techniques. For example, slope may be determined by applying linear regression techniques to samples within a timing window. In some cases, a moving window may be used within the timing window to evaluate slopes for subsets of the points within the timing window, e.g., based on linear regression techniques. In either case, the slope of the FFEGM signal for the timing window may be compared to a slope threshold. A flat or relatively small slope should be consistent with a baseline level that is not indicative of an actual cardiac event. If the slope is less than or equal to the threshold slope, processor 80 determines that the detected cardiac event should be classified as an oversensed event.

For variability, processor 80 may compute measures of statistical variation such as variance, standard deviation, interquartile range, or the like. Processor 80 may compare the variability measure for the FEEGM samples within the timing window to an applicable threshold. A low variability measure should be consistent with a baseline level that is not indicative of an actual cardiac event. If the variability measure is less than or equal to the threshold variability, processor 80 determines that the detected cardiac event should be classified as an oversensed event.

An oversensed R wave resets the R wave escape interval counter, which then outputs its count as the present R-R interval. Again, the R-R interval is used to control operation of the pacer timing and control module and cardioversion/defibrillation control module. The pacer timing and control module delivers a pacing pulse when the R-R interval exceeds a lower rate limit interval. The cardioversion/defibrillation control module delivers a cardioversion or defibrillation shock when short R-R intervals cause the VF counter to reach the NID level.

To prevent inhibited pacing or inappropriate shocks, when a detected cardiac event is identified as an oversensed event, processor 80 repairs the R-R interval. In particular, processor 80 does not provide the R-R interval to the pacer timing and control module and cardioversion/defibrillation control module. Instead, processor 80 sums the R-R interval with the next R-R interval produced by the R wave escape interval counter to produce a summed R-R interval. If the next R-R interval is also produced by an oversensed R wave, processor 80 again sums the summed R-R interval with the next R-R interval.

The process continues until processor 80 identifies an R-R interval that was not produced by an oversensed event. If there is a sequence of oversensed events, the R-R intervals produced by such events continue to be added until a legitimate event is detected, i.e., by determining that the corresponding FFEGM amplitude is greater than the threshold. At that time, processor 80 outputs the summed R-R interval as the R-R interval to be used by the pacer timing and control module and the cardioversion/defibrillation control module. Hence, the R-R interval output by processor 80 to the pacer timing and control module and the cardioversion/defibrillation control module may be a single R-R interval produced by a valid, detected R wave, or a summation of two or more R-R intervals produced by oversensed R waves with a final R-R interval produced by a valid, detected R wave.

Processor 80 repairs the R-R interval to represent actual cardiac events, rather than oversensed events, and performs the identification and remediation process on an event-by-event basis. Short R-R intervals (i.e., less than a threshold time period) may reside in a so-called VF zone that triggers processor 80 to increment the VF counter. When the VF counter reaches the NID threshold, the cardioversion/defibrillation control module causes electrical stimulation module 84 to deliver a shock. By summing R-R intervals based on invalid, oversensed events, processor 80 produces longer R-R intervals. In this manner, the lengths of R-R intervals that would have otherwise incremented the VF counter instead increase outside of the VF zone and not increment the VF counter.

Even if the identification techniques described in this disclosure do not identify all oversensed events, successful identification of a substantial number of such oversensed events may still be effective in preventing the VF counter from reached the NID threshold for delivery of a shock. As an illustration, even if the VF counter reaches 75% of the NID, it still would not trigger delivery of a shock, thereby avoiding delivery of inappropriate shocks in the presence of oversensing.

Likewise, to avoid syncope and asystole, the techniques for identification and remediation of oversensed events may produce R-R intervals of increased length. Again, by summing R-R intervals based on illegitimate R waves, the overall R-R interval provided to the pacer control and timing module of processor 80 may be longer and more accurately reflect actual cardiac events. If the R-R interval exceeds a lower rate interval limit, the pacer control and timing module controls electrical stimulation module 84 to deliver a pacing pulse. In the case of asystole, a continuous sequence of oversensed events would cause ICD 16 to withhold pacing for a pacemaker-dependent patient. During the withholding of pacing, there would be a flat isoelectric baseline on the FFEGM while noise was occurring on the NFEGM signal. Ordinarily, the isoelectric baseline would not exist during an actual, physiologic cardiac rhythm.

As described above, processor 80 compares the amplitude of the FFEGM in a timing window that corresponds to the detected cardiac event to a fixed or variable threshold to determine whether the FFEGM indicates a baseline level or an amplitude that correlates with, i.e., confirms, the detected cardiac event from the NFEGM signal. If the FFEGM amplitude is less than the threshold amplitude, processor 80 identifies the corresponding detected event from the NFEGM as an oversensed event and sums the resulting R-R interval with the next R-R interval. If the summed R-R interval of all the newly classified oversensed events reaches the lower rate interval, processor 80 controls electrical stimulation module 86 to deliver a bradycardia pacing pulse, thereby preventing asystole and syncope due to loss of pacing.

As alternatives to FFEGM amplitude, or in addition to FFEGM amplitude, processor 80 may be configured to analyze other characteristics such as slope or variability. For example, processor 80 may determine one or more slopes of the FFEGM signal within the timing window and compare the slope(s) to a fixed or variable threshold slope. If the slope is less than the threshold slope, then the corresponding detected cardiac event is identified as an oversensed event. Likewise, processor 80 may analyze the variability of the FFEGM signal within the timing window. If the variability exceeds the variability threshold, the processor 80 does not identify the detected cardiac event as an oversensed event. A variety of FFEGM signal characteristics may be evaluated in various combinations to aid in discriminating oversensed events from valid events. Accordingly, evaluation of amplitude, slope, or variability are described for purposes of illustration and without limitation.

In some implementations, when the R-R interval is modified due to oversensed events as described above, processor 80 may control stimulation module 86 to deliver two or more pacing pulses in quick succession. For example, two closely spaced pulses may be referred to as an overstimulation (OS) pacing pair. In some cases, the two or more pacing pulses may be delivered in quick succession (e.g., such that a second pulse follows a first pulse by about 5 to 100 milliseconds) using different stimulation vectors, i.e., different stimulation electrode configurations. In some cases, the current or voltage amplitude of the pacing pulses may be increased, relative to a normal amplitude, when oversensed events are detected. An increased amplitude may help capture the heart in the event of a lead fracture. For example, processor 80 may automatically control stimulation module 86 to increase the pacing amplitude when oversensed events are detected.

As an illustration, a first pacing pulse may be delivered via the ring and tip electrodes 40, 42 of RV lead 18, and a second pacing pulse may be delivered via a different electrode configuration on the same lead, on a different lead, within the same chamber or within a different chamber. Hence, various electrode configurations on different leads may be used, include unipolar or bipolar electrode combinations, to deliver stimulation via different stimulation vectors.

For example, the second pacing pulse could be delivered via the elongated coil electrode 62 of RV lead 18 and can electrode 58, or via other leads 18, 20, 22. For example, the second pacing pulse may be delivered via electrodes on LV lead 20 or atrial lead 22, in either bipolar or unipolar configurations. Additional pulses also may be delivered in some implementations, especially in the event the preceding pulse does not capture the heart to cause a ventricular depolarization. In general, delivery of multiple pacing pulses from different pacing vectors can provide redundancy in the event an oversensed event is indicative of a fractured conductor or other lead-relation condition that can impair reliable delivery of electrical stimulation pulses to the patient.

During each pacing pulse, electrical sensing module 86 of ICD 16 may monitor impedance on the electrode configurations used to deliver the pacing pulses to evaluate the integrity of the stimulation paths. If the impedance of a given stimulation path is out of range, i.e., below or above an expected impedance range, processor 80 may select a different electrode configuration to provide a different stimulation path. Hence, if stimulation is delivered via two or more vectors in quick succession, e.g., 5 to 100 milliseconds (ms) apart, and one or more of the vectors produces an out-of-range impedance (e.g., greater than about 2000 ohms), indicating a potential lead fault, processor 80 may control stimulation module 84 to deliver additional pulses via different vectors.

For example, after two pulses are delivered on first and second vectors, a third may be delivered on a different vector if one of the first and second vectors produces an out-of-range impedance. In addition, in some cases, processor 80 may control stimulation module 84 such that the vectors producing out-of-range impedances are not used for delivery of later pacing pulses. In each case, the impedance check can enhance the reliability of the pacing, particularly when combined with redundant deliver of multiple pacing pulses on different stimulation vectors.

As described above, according to some interval-based remediation techniques, processor 80 may modify R-R intervals when detected cardiac events are identified, in which case inappropriate shocks and/or inhibition of bradycardia pacing. As an alternative, other remediation techniques may be configured to directly trigger pacing when oversensed events are identified based on FFEGM data. According to one example of an alternative timeout-based remediation technique, if fibrillation events are sensed in the NFEGM signal, processor 80 may evaluate one or more FFEGM characteristics such as amplitude, slope, or variability, as described above, to determine whether the events are oversensed events. A fibrillation event may be a detected cardiac event such as an R wave that indicates a sensed fibrillation event, e.g., based on a short R-R interval or R-R variability (e.g., irregularity of successive R-R interval lengths).

As one illustration, when two consecutive detected fibrillation events such as detected R waves produce a short R-R interval or R-R variability, processor 80 compares the amplitude of the FFEGM within a timing window coincident with the cardiac event detected on the NFEGM, as described above with respect to the interval-based remediation technique. If the FFEGM amplitude is greater than the threshold, processor 80 determines that the FFEGM amplitudes corresponding to each of the two consecutive detected fibrillation events are both below a fixed or variable threshold, then the processor identifies that the detected cardiac events as oversensed events.

Upon identification of the oversensed events, processor 80 controls electrical stimulation module 84 to deliver one or more bradycardia pacing pulses after the next detected cardiac event that occurs following a timeout period running from the previous non-oversensed cardiac event, e.g., 5 to 100 milliseconds (ms) after the detected cardiac event. For example, processor 80 may be configured to cause electrical stimulation module 84 to deliver a pacing pulse in synchronization with the next detected R-wave following expiration of the timeout period running from a previous non-oversensed ventricular R-wave or ventricular pace, or from a previously sensed atrial P-wave, atrial pace, or atrial refractory event, depending on whether ICD 16 is configured as a single-chamber or multi-chamber device.

As an illustration, the timeout period may be selected to be a two-second timeout period, which corresponds to a 30 beats-per-minute lower rate interval for pacing. Delivering pacing with a timeout period that corresponds to the lower rate interval when oversensed events are identified may help to avoid syncope and asystole. In some implementations, as described above, two or more pacing pulses may be delivered in quick succession via different stimulation vectors provided by different stimulation electrode configurations. For each pacing pulse, ICD 16 may obtain an impedance measurement of the stimulation path defined by the stimulation electrode configuration, as described above. Again, three, four or more pulses may be delivered in some instances, particularly when the impedance measurement indicates out-of-range impedance values (e.g., impedance values greater than 2000 ohms).

For example, a first pacing pulse may be delivered via ring electrode 40 and tip electrode 42 of RV lead 18, and a second pacing pulse may be delivered through an alternative electrode pair, such as elongated coil electrode 62 on RV lead 18 and can electrode 58. Alternatively, the second pacing pulse may be delivered via different electrode configurations on the same lead, on a different lead, within the same chamber or within a different chamber. In each case, the second pacing pulse may be considered a safety, backup or redundant pulse that provides redundancy in the event one or more conductors associated with the first electrode configuration are fractured or otherwise impaired, as possibly indicated by the identification of oversensed events obtained in the NFEGM, which use the same set of electrodes as the primary sensing electrode configuration and primary stimulation electrode configuration, in some cases.

According to some examples, processor 80 may deliver the pacing pulses in response to the identified oversensed events on a selective basis according to whether the patient 12 is generally a pacemaker-dependent patient. For example, if the patient 12 has required bradycardia pacing on a greater than 50% basis (i.e., for more than 50% of beats) since the last programming session, then processor 80 may activate this remediation technique to deliver the pacing pulse or pulses when oversensed events are detected. The last programming session may be the last session, remote or in-clinic, during which the ICD 16 was interrogated and/or programmed by an external programmer. If the patient 12 has required pacing for less than 50% of the time, in some implementations, processor 80 does not activate timeout-based remediation for oversensed events.

The timeout period may run from a previous non-oversensed event, or at least an event that processor 80 did not identify as oversensed. For a dual- or multi-chamber ICD, for example, the timeout period may run from a previous non-oversensed atrial cardiac event (P wave) or a previous non-oversensed ventricular cardiac event (R wave). The P waves and R waves may be detected using respective NFEGMS obtained from primary sensing electrode configurations, such as a combination of the tip electrode 40 and ring electrode 42 of RV lead 18 for R waves or a combination of the ring electrode 48 and tip electrode 50 of right atrial (RA) lead 22 for the P wave.

Identification of oversensing may be based on the amplitude of other characteristics of a FFEGM signal. If two consecutive oversensed cardiac events are identified during this timeout period, then one or more pacing pulses are delivered upon detection of the next atrial (P wave, pace, or refractory event) or ventricular event (R wave or pace) detected following expiration of the timeout period. Again, the oversensed events may be ventricular depolarizations (R waves) indicating short or varied R-R intervals. The next event may be an oversensed event or a non-oversensed event.

For a single-chamber ICD, in which case atrial events are not available, the timeout period may run from a previous non-oversensed ventricular cardiac event (R wave). The R waves may be detected using respective NFEGMs obtained from a primary sensing electrode configuration, such as a combination of the tip electrode 40 and ring electrode 42 of RV lead 18. If two consecutive oversensed cardiac events are identified during this timeout period, then one or more pacing pulses are delivered upon expiration of the timeout period or upon detection of the next ventricular event (R wave) detected following expiration of the timeout period. The next event may be an oversensed event or a non-oversensed event. In each case, for a single-, dual- or multi-chamber ICD, impedance can be monitored during each pacing pulse to evaluate the integrity of the stimulation path.

In addition to delivering pacing pulses in the presence of oversensed events, for timeout-based remediation technique, processor 80 also may be configured to inhibit delivery of cardioversion or defibrillation shocks. For example, processor 80 may apply a timeout-based remediation technique for delivery of pacing pulses and an interval-based remediation technique for inhibition of cardioversion and defibrillation shocks. In other words, processor 80 may control electrical stimulation module 84 to deliver the pacing pulses upon expiration of the timeout period or immediately following the next detected cardiac event (e.g., R wave) after expiration of the timeout period, and also repair oversensed events to length R-R intervals and thereby prolong ascension of the VF count toward the NID, thereby inhibiting inappropriate shocks.

Processor 80 may store in memory 82 marker channel data indicating events detected for each NFEGM and FFEGM, as well as addition to raw, statistical or processed NFEGM and FFEGM values. The marker channel data may record all detected cardiac events to permit a clinician to review the detected data and possibly identify oversensing and factors such as lead-related conditions that may cause oversensing. Processor 80 may also store parametric data within memory 82. Parametric data may include, for example, impedance measurements, trends of impedance measurements, or statistical or other processed values determined based on impedance measurements. Processor 80 may provide marker channel data, EGM data, and parametric data 90 to programmer 24 or other external devices via telemetry module 88. A clinician may review such data to evaluate oversensing and identify potential lead-related conditions or other noise sources.

Figure 5:
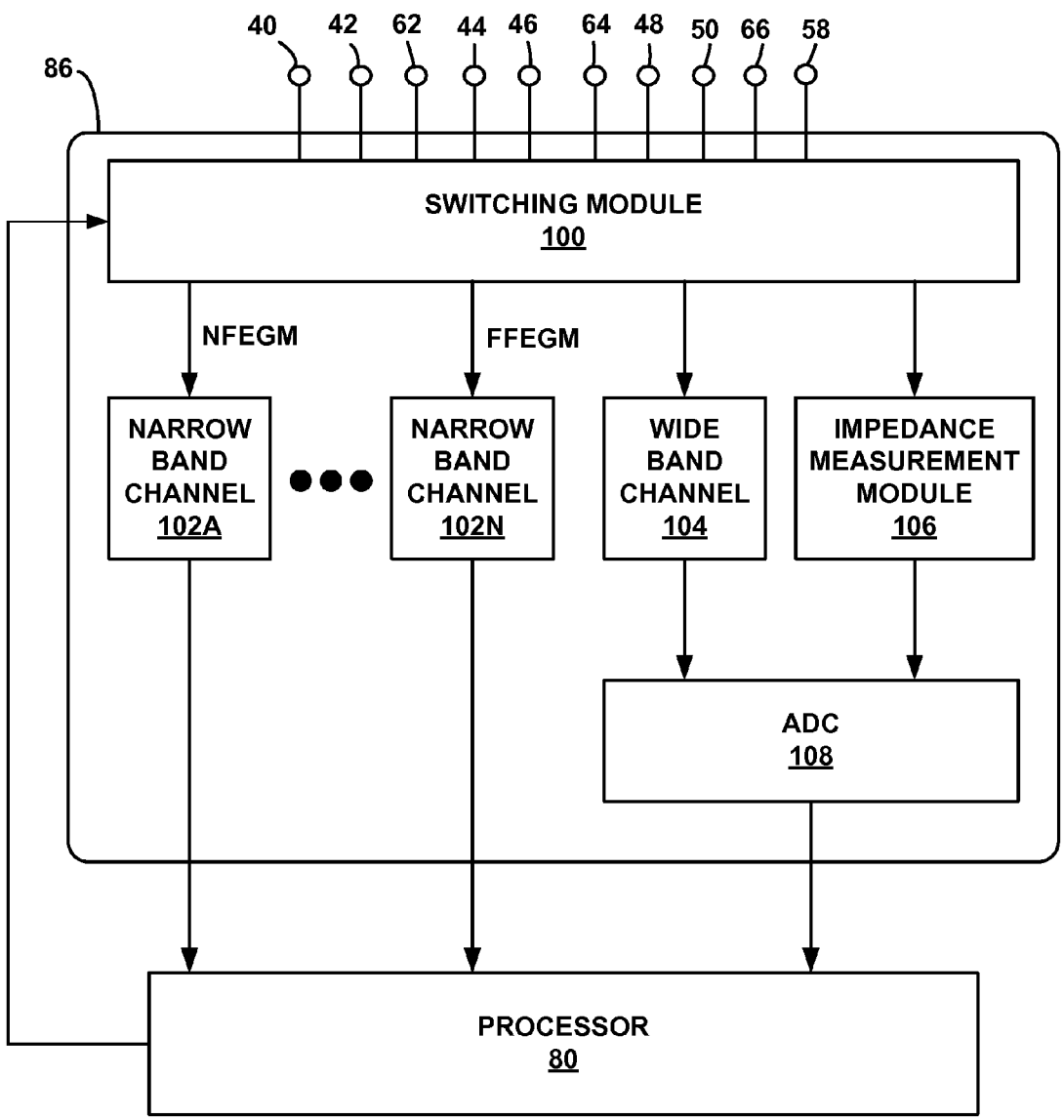
FIG. 5 is a functional block diagram illustrating an example electrical sensing module of the ICD of FIG. 1.

FIG. 5 is a block diagram of an example configuration of electrical sensing module 86. Sensing module 86 may be configured to acquire a first cardiac signal via a first sense electrode configuration (e.g., a NFEGM signal), and acquire a second cardiac signal via a second sense electrode configuration (e.g., a FFEGM signal), as will be described. As shown in FIG. 5, electrical sensing module 86 may include multiple components including a switching module 100, narrow band channels 102A to 102N (collectively "narrow band channels 102"), wide band channel 104, impedance measurement module 106, and analog to digital converter (ADC) 108. Switching module 100 may, based on control signals from processor 80, control which of electrodes 40, 42, 44, 46, 48, 50, 58, 62, 64 and 66 is coupled to which of channels 102 and 104 and impedance measurement module 106, at any given time.

Each of narrow band channels 102 receives an EGM signal. For example, some narrow band channels 102 may receive NFEGM signals and other narrow band channels may receive FFEGM signals. Switching module 100 may be controlled to connect particular sensing electrode configurations across selected narrow band channels 102. Each narrow band channel 102 may comprise a narrow band filtered sense-amplifier that compares the obtained signal to a threshold or other criteria. If the filtered and amplified signal is greater than the threshold, the narrow band channel indicates that a certain electrical cardiac event (e.g., an R wave or P wave) has occurred. Processor 80 may use the detection from sensing module 86 to detect cardiac events in the first and second cardiac signals, e.g., detected P waves or R waves in the NFEGM and FFEGM signals, and may determine frequencies of, or intervals between, the detected events. Narrow band channels 102 may have distinct functions. For example, some narrow band channels may be used to either detect either atrial or ventricular events.

In one example, at least one narrow band channel 102 may include an R-wave amplifier that receives signals from the primary sensing electrode configuration of electrodes 40 and 42 or RV lead 18, which are used for sensing and/or pacing in right ventricle 28 of heart 12. Another narrow band channel 102 may include another R-wave amplifier that receives signals from the sensing electrode configuration of electrodes 44 and 46 of LV lead 20, which are used for sensing and/or pacing proximate to left ventricle 32 of heart 12. Using the outputs of the R-wave amplifiers, processor 80 may detect R-wave events in NFEGM and/or FFEGM signals. In some examples, the R-wave amplifiers may take the form of an automatic gain controlled amplifier that provides an adjustable sensing threshold as a function of the measured R-wave amplitude of the heart rhythm.

In addition, in some examples, a narrow band channel 102 may include a P-wave amplifier that receives signals from electrodes 48 and 50 of RA lead 22, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Using the output of the P-wave amplifier, processor 80 may detect P-wave events in NFEGM and/or FFEGM signals. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels 102 of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12. Again, switching module 100 may be selectively controlled to couple narrow band channels 102 to different sensing electrode configurations to provide various NFEGMs and FFEGMs.

Wide band channel 104 may comprise an amplifier with a relatively wider pass band than the R-wave or P-wave amplifiers. Signals from the sensing electrode configuration that is selected for coupling to this wide-band amplifier may be converted to multi-bit digital signals by ADC 108. In some examples, processor 80 may store digitized versions of signals from wide band channel 104 in memory 82 as EGMs. In some examples, the storage of such EGMs in memory 82 may be under the control of a direct memory access (DMA) circuit. Processor 80 may use signals from wide band channel 104 to analyze FFEGM signal characteristics within a timing window coincident with a cardiac event.

Processor 80 may detect cardiac events in NFEGM and FFEGM signals based on events detected by narrow band channels 102 or based on analysis of the sensed signals. In some examples, processor 80 may employ digital signal analysis techniques to characterize the digitized signals from wide band channel 104 to, for example, detect and classify the patient's heart rhythm. Processor 80 may detect and classify the patient's heart rhythm by employing any of the numerous signal processing methodologies known in the art. Further, in some examples, processor 80 may analyze the morphology of the digitized signals from wide band channel 104 to distinguish between noise and cardiac depolarizations. Based on such morphological analysis, processor may detect a suspected oversensed event.

In some examples, sensing module 86 and/or processor 80 are capable of collecting, measuring, and/or calculating impedance data for any of a variety of electrical paths that include two or more of electrodes 40, 42, 44, 46, 48, 50, 58, 62, 64 and 66. In such examples, impedance measurement module 106 may measure electrical parameter values during delivery of an electrical signal between at least two of the electrodes. As discussed above, for example, impedance measurement module 106 may be used to measure impedance during delivery of one or more pacing pulses in order to evaluate the integrity of the stimulation paths and permit switching to alternate paths in the event impedance values are out-of-range, indicating possible lead faults.

Processor 80 may control electrical stimulation module 84 to deliver an electrical impedance measurement electrical signal between selected electrodes. Processor 80 may determine impedance values based on parameter values measured by impedance measurement module 106. In particular, ADC 108 may digitize parameter values measured by impedance measurement module 106, and processor 80 may determine impedance values based on the digitized parameter values and store the impedance values as parametric data 90 in memory 82.

In some examples, processor 80 may perform an impedance measurement by controlling delivery, from electrical stimulation module 84, of a voltage pulse between first and second electrodes. Impedance measurement module 106 may measure a resulting current, and processor 80 may calculate a resistance based upon the voltage amplitude of the pulse and the measured amplitude of the resulting current as digitized by ADC 108. In other examples, processor 80 may perform an impedance measurement by controlling delivery, from electrical stimulation module 84, of a current pulse between first and second electrodes. Impedance measurement module 106 may measure a resulting voltage, and processor 80 may calculate a resistance based upon the current amplitude of the pulse and the measured amplitude of the resulting voltage as digitized by ADC 108. Impedance measurement module 106 may include circuitry for measuring amplitudes of resulting currents or voltages, such as sample and hold circuitry.

In these examples of performing impedance measurements, electrical stimulation module 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. ICD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, ICD 16 may collect impedance values that include both a resistive and a reactive (i.e., phase) component. In such cases, ICD 16 may measure impedance during delivery of a sinusoidal or other time varying signal by electrical stimulation module 84, for example. Thus, as used herein, the term "impedance" is used in a broad sense to indicate any collected, measured, and/or calculated value that may include one or both of resistive and reactive components. Impedance data may include actual, measured impedance values, or may include values that can be used to calculate impedance (such as current and/or voltage values).

In one embodiment, processor 80 may analyze the measured impedance values, and may compare these values, or other computed values, to determined thresholds or ranges and identify any possible conditions with one or more electrical paths that include two or more of the electrodes. For example, processor 80 may, as a result of one or more comparisons, determine that one or more of leads 18, 20, and 22 has a lead-related condition, or more specifically that one or more electrodes or associated conductors within the leads may have an integrity condition. Processor 80 may send impedance measurement and/or analysis data to programmer 24 via telemetry module 88.

Figure 6:
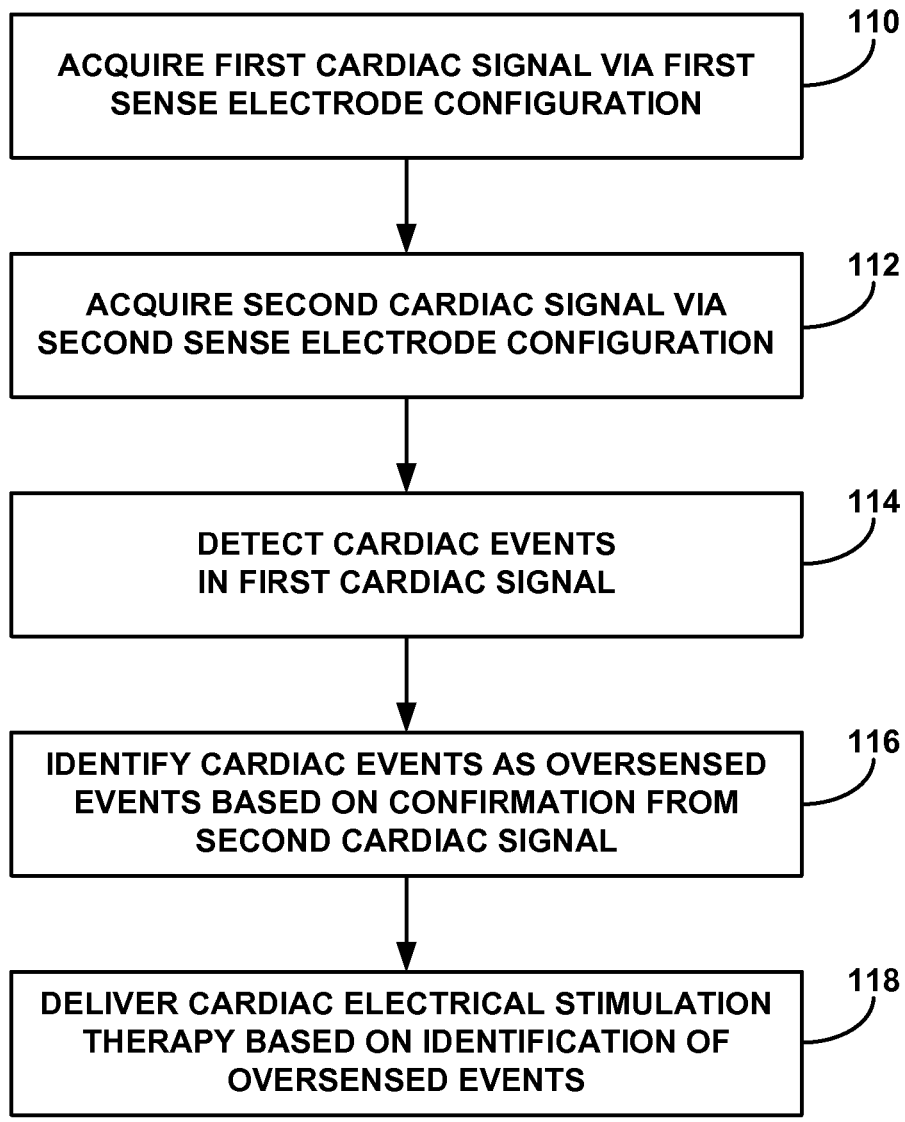
FIG. 6 is a flow diagram illustrating a method for identification and remediation of oversensed cardiac event.

FIG. 6 is a flow diagram illustrating a method for identification and remediation of oversensed cardiac event. In the example of FIG. 6, an ICD 16 acquires a first cardiac signal via a first sense electrode configuration (110). For example, as described above in this disclosure, ICD 16 may obtain a NFEGM signal via a primary sensing electrode configuration such as ring electrode 40 and tip electrode 42 of RV lead 18. In addition, ICD 16 acquires a second cardiac signal via a second sense electrode configuration (112). For example, ICD 16 may obtain a FFEGM signal via a different sensing electrode configuration, such as elongated coil electrode 62 of RV lead 16 and can electrode 58. A coil-can electrode configuration may provide a FFEGM signal that is unaffected by lead noise on the ring-tip electrode configuration, particularly in a true bipolar lead in which the coil uses a different conductor than the conductors used for the tip and ring electrodes. A variety of different sensing electrode configurations may be used to obtain the NFEGM and FFEGM signals.

Using the first cardiac signal, e.g., the NFEGM signal, ICD 16 detects cardiac events (114). For example, ICD 16 may detect P wave events and/or R wave events, some of which may be oversensed events. ICD 16 identifies at least some of the cardiac events as oversensed events based on confirmation from the second cardiac signal (116). For example, ICD 16 may compare an amplitude or other characteristic of the FFEGM signal to a threshold or other criterion to determine whether that FFEGM signal characteristic correlates with the detected event. If not, e.g., if the amplitude is less than an applicable threshold, ICD 16 identifies the corresponding event as an oversensed event.

If a detected cardiac event such as an R wave is identified as an oversensed event based on the FFEGM signal, ICD 16 proceeds to delivery cardiac electrical stimulation therapy based on identification of the oversensed events (118). For example, ICD 16 may apply interval-based remediation techniques as described in this disclosure to inhibit inappropriate shocks and/or prevent inappropriate inhibition of bradycardia pacing. Alternatively, ICD 16 may apply timeout-based remediation techniques to actively deliver one or more bradycardia pacing pulses following expiration of a timeout period. In either case, ICD 16 may deliver two or more pacing pulses in quick succession e.g., 5 to 100 milliseconds (ms) apart, via different stimulation vectors defined by different stimulation electrode configurations. In addition, ICD 16 may measure impedance values of the stimulation vectors and deliver pacing via different vectors if impedance values are out-of-range.

Figure 7:
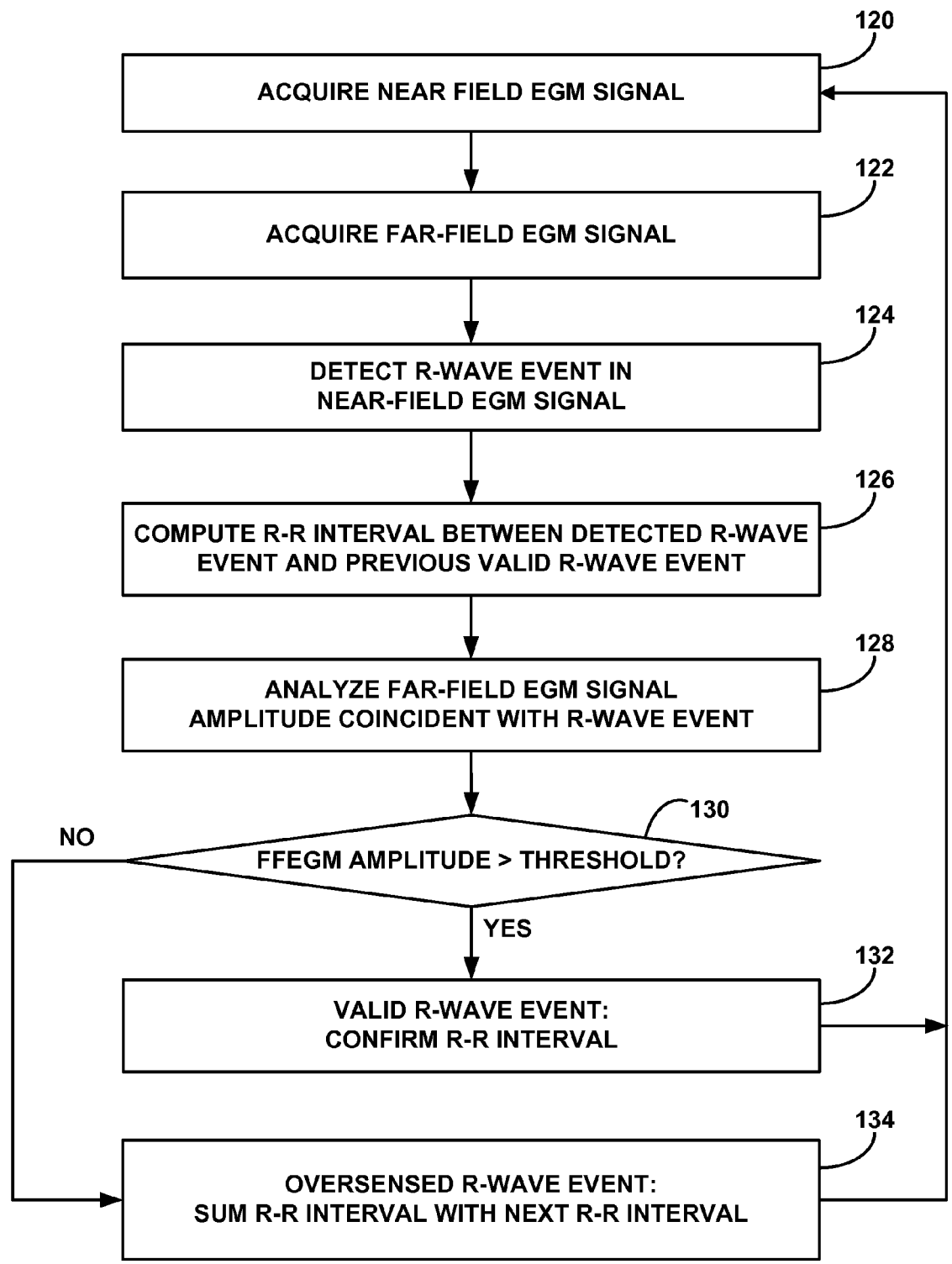
FIG. 7 is a flow diagram illustrating an example of the use of far-field electrogram (FFEGM) amplitude analysis in the method of FIG. 6.

FIG. 7 is a flow diagram illustrating an example of the use of far-field electrogram (FFEGM) amplitude analysis in the method of FIG. 6. In particular, FIG. 7 illustrates the use of an interval-based remediation technique to avoid inappropriate shocks and prevent inhibition of bradycardia pacing when oversensed events are detected. As shown in FIG. 7, ICD 16 acquires a NFEGM signal via a first sense electrode configuration (120) and obtains a FFEGM signal via a second sense electrode configuration (122). ICD 16 detects an R-wave event in the NFEGM signal, e.g., via one of the narrow-band sense channels 102. ICD 16 computes an R-R interval between the detected R wave event and a previous non-oversensed R wave event, i.e., an R wave event that was not identified as oversensed and may be assumed to be valid. The R-R interval may be computed, for example, based on the count produced by the ventricular escape interval counter when the detected R wave event resets the counter.

Upon analyzing the amplitude of the FFEGM signal coincident with the detected R-wave event (128), ICD 16 determines whether the FEEGM amplitude is greater than a fixed or variable threshold value (130). As an example, ICD 16 may analyze a digitized version of the FFEGM signal obtained via wideband channel 104. The FFEGM amplitude may be determined, as described above, based on a difference between a maximum amplitude and minimum amplitude within a timing window (e.g., 200 milliesconds), which may be centered at the time the cardiac event was detected in the NFEGM signal. Again, other types of FFEGM signal characteristics may be evaluated as alternatives or in combination with FFEGM amplitude. Also, FFEGM amplitude may be calculated in other ways.

In any event, in the example of FIG. 7, if the FFEGM amplitude is greater than the threshold, ICD 16 determines that the FFEGM signal does not indicate that the detected cardiac event is an oversensed event. In this case, ICD 16 may determine that the detected R wave event is a valid event and confirm the R-R interval created by the detected R wave event in conjunction with the previous non-oversensed R wave event (132). Again, an oversensed event is a detected cardiac event that does not represent normal, electrical physiological activity of the heart, but rather is caused by noise such as lead-related noise, EMI, or myopotentials.

Although the R wave event is indicated as valid in the example of FIG. 7, the R wave event may in fact be legitimate or illegitimate. The identification process may not correctly identify every oversensed event, but may identify a sufficient number of them to reduce the likelihood of inappropriate shocks or inhibited pacing. Accordingly, the R wave event may be considered valid for purposes of the remediation technique, but it is not necessarily important that the validity of the event is known with certainty.

With further reference to FIG. 7, if the R-R interval is confirmed, ICD 16 does not adjust the current R-R interval. Instead, the R-R interval is provided to the pacer timing and control module and cardioversion/defibrillation control module of processor 80 for use in determining whether to deliver pacing pulses or cardioversion or defibrillation shocks, respectively. In this case, ICD 16 acquires the next NFEGM signal (120) and repeats the process. If the FFEGM amplitude is not greater than the threshold (130), however, ICD 16 determines that the detected R wave event is an oversensed R wave event and sums the current R-R interval with the next R-R interval (134). In particular, ICD 16 sums the R-R interval with the next R-R interval extending between the detected cardiac event and the next cardiac event detected in the NFEGM by ICD 16.

As an illustration, if the first R-R interval between a first, non-oversensed R wave and a second, oversensed R-wave is x milliseconds (ms), and a second R-R interval between the second, oversensed R wave and a next, third non-oversensed R wave is y ms, then ICD 16 sums the first and second R-R intervals to produce a third R-R interval equal to x+y ms. If the third R wave is also oversensed, then ICD 16 sums the third R-R interval with the next R-R interval extending between the third, oversensed R wave and a next, fourth R wave. Following identification of an oversensed R wave event, ICD 16 proceeds to acquire the next NFEGM signal. This process continues until ICD 16 identifies an R wave that is not oversensed, per the FFEGM amplitude comparison, in which case, the ICD computes the final R-R interval as the sum of the oversensed R-R intervals leading up to the non-oversensed event. Then, ICD 16 proceeds to compute the next R-R interval and repeats the process.

Figure 8:
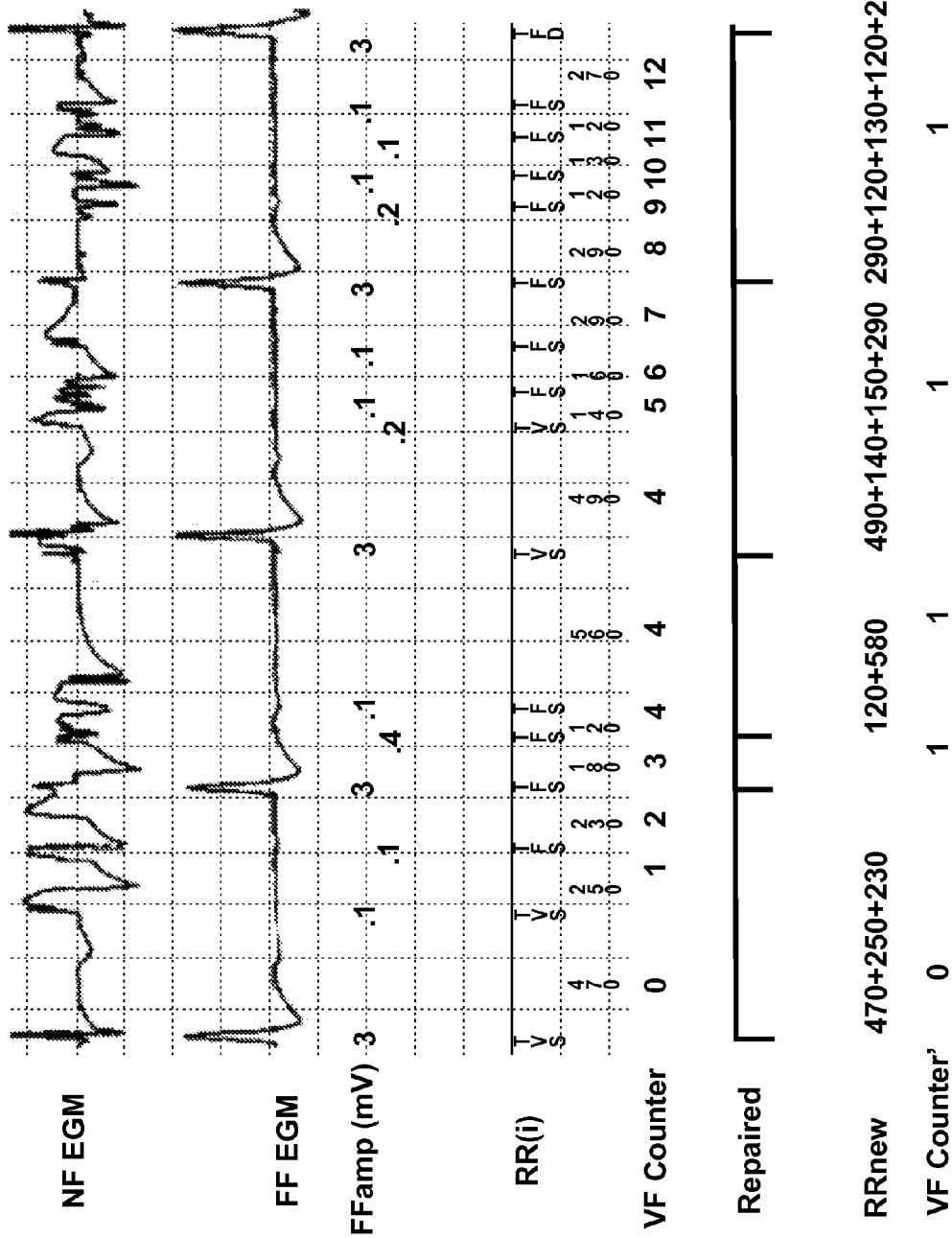
FIG. 8 is a graph illustrating a technique for identification and remediation of oversensed cardiac events using an FFEGM to inhibit delivery of an inappropriate defibrillation shock.

FIG. 8 is a graph illustrating a technique for identification and remediation of oversensed cardiac events using an FFEGM to inhibit delivery of a defibrillation shock. In the example of FIG. 8, the NFEGM signal represents a signal obtained via a primary sensing electrode configuration such as ring electrode 40 and tip electrode 42 of RV lead 18. The FFEGM signal represents a signal obtained via a different sensing electrode configuration such as elongated coil electrode 62 and can electrode 58. The FFamp (mV) line shows FFEGM signal amplitude values calculated within timing windows corresponding to various cardiac events detected in the NFEGM signal.

The RR(i) line includes the marker channel data for the NFEGM signal, including ventricular sensed (VS) depolarization, i.e., detected R waves, ventricular sensed fibrillations (FS), i.e., detected R waves occurring with short R-R intervals or varied R-R intervals. The RR(i) line also indicates respective R-R intervals between successively detected R waves in the NFEGM, expressed in milliseconds (ms). For example, the first five R waves produce R-R intervals of 470, 250, 230, 180, and 120 ms, respectively. The 250, 230 and 180 ms R-R intervals are shorter than a threshold interval of 300 ms, and therefore are recorded in the marker channel data as FS events rather than just VS events.

The VF counter line indicates the cumulative VF count as the VF counter increments with each short R-R interval. For example, the 250, 230, and 180 ms intervals cause the VF count to increment from 0 to 3. In some cases, the VF count may hold steady or decrement in response to longer R-R intervals. As indicated in FIG. 8, for example, where the VF counter remains at 4 over three consecutive R-R intervals. In FIG. 8, ICD 16 applies techniques for identification and remediation of oversensed events. The Repaired line indicates R-R intervals that are modified based on identification of oversensed R wave events in the NFEGM signal based on FFEGM amplitudes. The RRnew line indicates the resulting R-R interval values upon repair of the R-R intervals.

For example, for the first and fourth R waves in the NFEGM signal, ICD 16 determines that the amplitude of the FFEGM signal is approximately 3 millivolts (mV), which is greater than an applicable threshold. In this illustration, the threshold amplitude is assumed to be approximately 0.3 mV. Because the 3 mV amplitudes of the FFEGM signal are both above the 0.3 mV threshold amplitude, the FFEGM signal indicates that the first and fourth R waves in the NFEGM signal are not likely oversensed events. However, the FFEGM signal amplitude is only 0.1 mV for the second and third R wave events in the NFEGM signal. In this case, ICD 16 identifies the second and third R waves as oversensed events.

Upon identification of the second R wave event as an oversensed event, ICD 16 sums the R-R interval between the first and second R waves (470 ms) with the next R-R interval (250 ms) to form a repaired R-R interval. However, ICD further sums this repaired R-R interval with the R-R interval (230 ms) between the third oversensed R wave and fourth, non-oversensed event to form the final repaired R-R interval of 470+250+230=950 ms. Although the fourth event was identified as an FS event, it would not have been if the second and third events would not have been oversensed.

The repaired R-R interval restores the R-R interval data to be close to its proper length. The R-R interval data does not need to be exactly the proper length in order to provide benefit. Using the repaired R-R interval data, the repaired VF counter in the VF Counter' line does not increment in response to all of the erroneously short R-R intervals caused by the oversensed R waves in the NFEGM. Consequently, the VF Counter' does not reach the NID level to trigger delivery of an inappropriate defibrillation shock. In the example of FIG. 8, at the far right of the VF counter, FD indicates detection of ventricular fibrillation in response to the VF Count meeting the NID level of 12 as a result of multiple increments due to oversensed events. A shock may be delivered after pertinent capacitors are charged. In the repaired VF Counter', however, the VF count does not even approach the NID level of 12. As a result, the interval-based remediation technique shown in FIG. 8 and described in this disclosure is effective in avoiding delivery of an inappropriate defibrillation shock.

Figure 9:
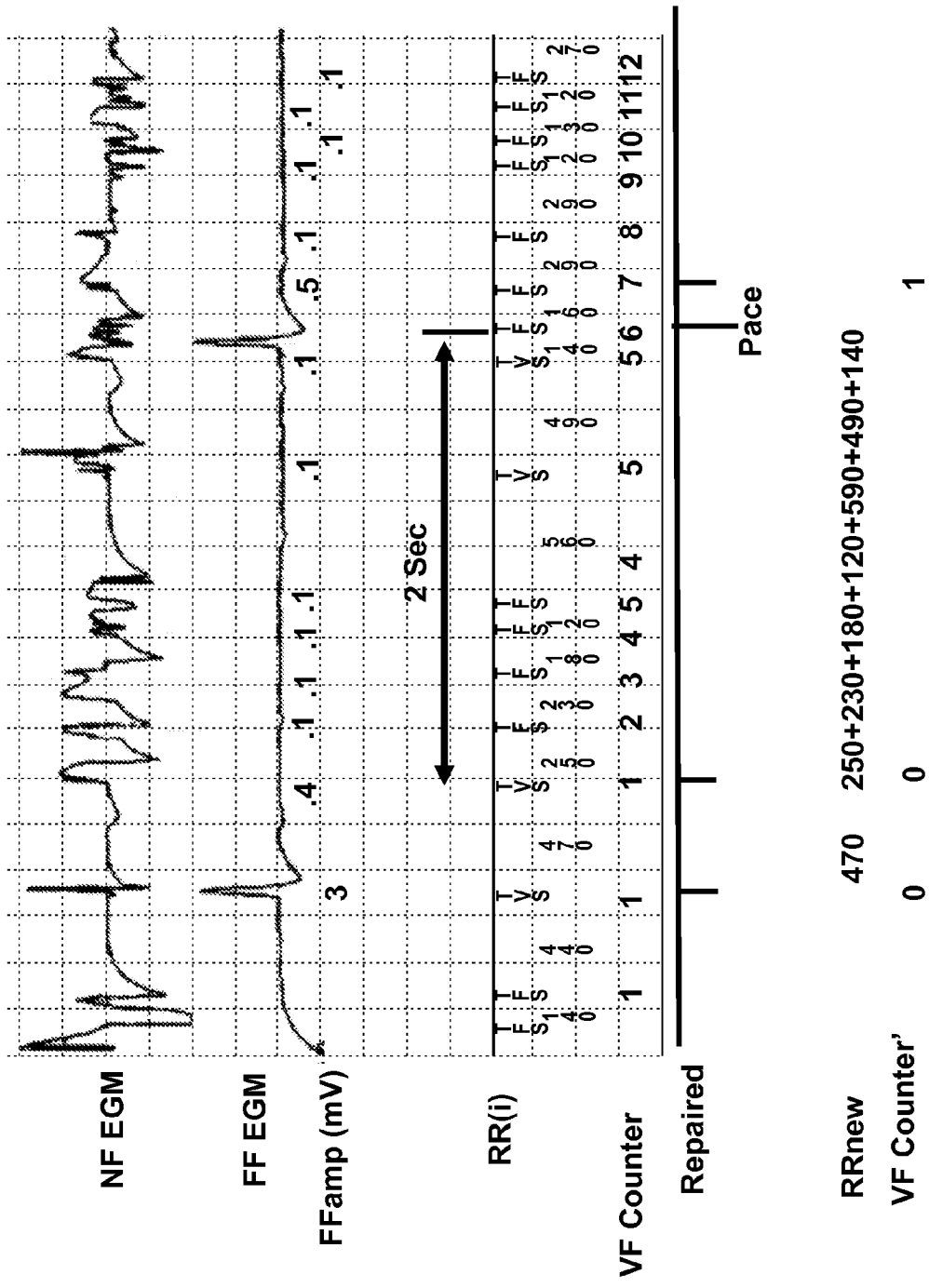
FIG. 9 is a graph illustrating a technique for identification and remediation of oversensed cardiac events using an FFEGM to permit delivery of a bradycardia pacing pulse.

FIG. 9 is a graph illustrating a technique for identification and remediation of oversensed cardiac events using an FFEGM to permit delivery of a bradycardia pacing pulse. In addition to preventing inappropriate incrementing of the VF counter, the repaired R-R interval is able to increase to a length that reflects actual physiological electrical activity in the heart, instead of oversensed activity. When the repaired R-R interval exceeds the lower rate interval, e.g., two seconds, ICD 16 is able to deliver a pacing pulse to reduce the risk of syncope and asystole, particularly for a pacemaker-dependent patient. FIG. 9 is similar to FIG. 8 in that it shows NFEGM, FFEGM, FFamp (mV), RR(i), VF Counter, Repaired RR, RRnew, and VF Counter' lines. However, FIG. 9 illustrates the operation of interval-based remediation in preventing inappropriate inhibition of pacing.

As shown in FIG. 9, in addition to avoiding inappropriate increases in the VF Counter', the repaired R-R intervals and resulting RRnew values are lengthened. In some cases, if a legitimate ventricular depolarization does not occur in sufficient time, the R-R interval may exceed a lower rate interval. In the example of FIG. 9, the fourth through tenth R waves events include R wave events that create short R-R intervals RR(i). However, many of the events are oversensed, as indicated by the corresponding FFEGM amplitude (FFamp) values. In reality, from the fourth to the ninth event, the patient does not experience an actual ventricular depolarization and is at risk of syncope and asystole.

The interval-based remediation technique repairs the R-R interval from the fourth through the ninth event such that the new R-R interval value (RRnew) exceeds the lower rate limit interval, e.g., two seconds in the example of FIG. 9. In particular, the various R-R intervals (250, 230, 180, 120, 590, 490, 140) are summed by ICD 16 to produce a repaired R-R interval of greater than or equal to two seconds, which triggers delivery of a bradycardia pacing pulse, shown in the Repaired line as "Pace." The summed R-R interval eliminates one or more non-physiological short R-R intervals. A sequence of oversensed events during asystole sum to the lower pacing rate interval for delivery of a pacing pulse. Again, the pace may be a single pace or multiple paces delivered via multiple stimulation vectors defined by different stimulation electrode configurations. In contrast, without remediation of the oversensed events, there is no pace delivered in the RR(i) line because the R-R interval never becomes large enough to exceed the lower rate limit (e.g., 2 seconds).

Figure 10:
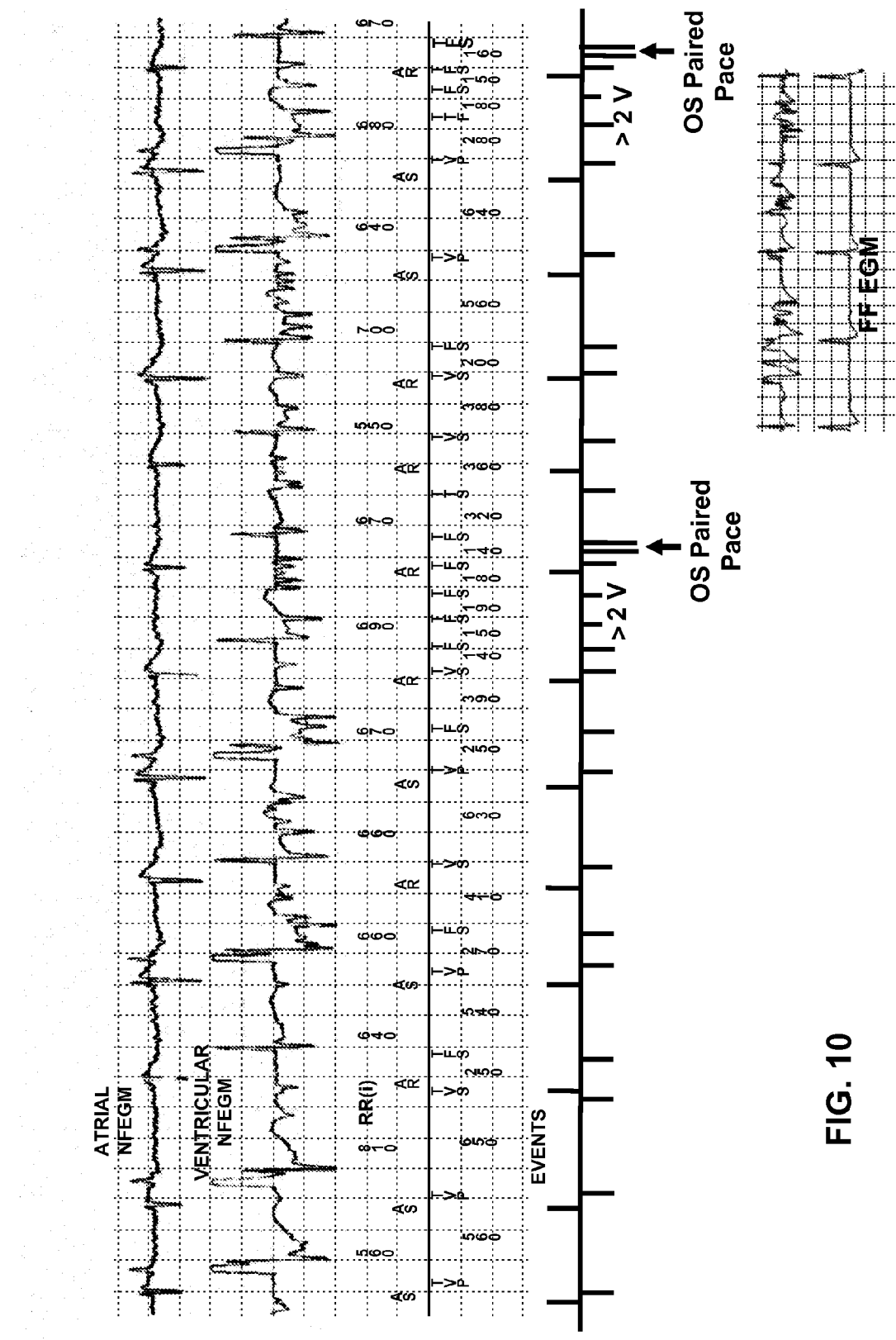
FIG. 10 is a graph illustrating another technique for identification and remediation of oversensed cardiac events using an FFEGM to permit delivery of a bradycardia pacing pulse and immediate backup pacing pulse.

FIG. 10 is a graph illustrating another technique for identification and remediation of oversensed cardiac events using an FFEGM to permit delivery of a bradycardia pacing pulse. More particularly, FIG. 10 shows an atrial sensing-based remediation technique. In general, an ICD may trigger pacing if at least a minimum number of oversensed R wave events are identified in a given period. For example, in a dual chamber ICD, having atrial and ventricular leads, the ICD may trigger pacing if at least a minimum number of oversensed R wave events are identified since a previous detected atrial event, i.e., a detected P wave, atrial pace or atrial refractory event.

The ICD 16 may deliver a pacing pulse after the next detected atrial event, at the programmed AV interval (e.g., 250 milliseconds (ms) after the detected atrial event). In some cases, two or more pacing pulses may be delivered as multiple, short coupled pacing pulses in quick succession, e.g., where a second pulses if deliver 5 to 100 milliseconds (ms) after the initial pacing pulse, using different stimulation vectors (e.g., bipolar, unipolar, left ventricular). During, before or after delivery of each pacing pulse, impedance can be monitored to evaluate the integrity of the stimulation path. Impedance monitoring can be programmed or automatically activated for pacemaker dependent patients, e.g., patients with more than 50% paced beats.

In the example of FIG. 10, the top line indicates an atrial NFEGM indicating P waves, the second line indicates a ventricular NFEGM indicating R waves, and the third line RR(i) indicates atrial P wave events and ventricular R wave events, along with atrial PP interval values and R-R interval values. Atrial events are on top of the horizontal dividing line and ventricular events are on the bottom. AS indicates a sensed P wave, AR indicates an atrial refractory event, VP indicates a ventricular pace, VS indicates a sensed ventricular R wave, and FS indicates a ventricular fibrillation sensed event.

FIG. 10 assumes that ICD 16 is a dual or triple chamber ICD with atrial sensing capabilities via an atrial lead 22 deployed in the right atrium. In FIG. 10, the fourth line Events indicates the timing of the atrial and ventricular detected events shown in the third line. In the lower right corner, FIG. 10 shows an example of a FFEGM coincident with a portion of a ventricular NFEGM as shown in the second line. In the example of FIG. 10, if greater than n (e.g., n=2) consecutive ventricular fibrillation sense (FS) events are detected since a previous atrial event (AS), ICD 16 determines whether the FFEGM signal amplitude is greater than a particular threshold value (e.g., 1 mV in the example of FIG. 10) at a time coincident with any or all of the ventricular events.

If not, ICD 16 identifies an oversensing condition, and causes a pacing pulse to be delivered after the next atrial event. The next atrial event may be, for example, an AS, AR or AP event. ICD 16 may deliver the initial pacing pulse according to a program (e.g., 250 ms after an atrial event) with a backup pacing pulse followed shortly after the initial pacing pulse, e.g., within 5 to 100 milliseconds (ms) following the initial pacing pulse. In the example of FIG. 10, if the FFEGM amplitude is less than the threshold, indicating oversensing, the pacing pulse is delivered as a pair of pacing pulses (OS Paired Pace) in quick succession (e.g., about 5 to about 100 ms apart) to provide overstimulation (OS) via multiple stimulation vectors. The first pulse may be delivered via an electrode configuration formed, for example, by ring electrode 40 and tip electrode 42. A second, safety pace may be delivered through a second electrode configuration, such as coil electrode 62 and can electrode 58, or other electrode configurations such as configurations including electrodes on the left ventricular lead. In some cases, the current or voltage amplitudes of the pacing pulses may be increased, relative to a normal amplitude, when oversensed events are detected, e.g., to improve the probability of capturing the heart in the event of the oversensed events are caused by lead fracture.

Again, as alternatives to FFEGM amplitude, or additionally, ICD 16 may consider slope, variability, or other characteristics. Another example characteristic may be a cumulative amplitude of the portions of the FFEGM signal corresponding to the FS events, in comparison to a particular threshold value. As discussed above, ICD 16 may measure impedance on the stimulation vectors and, if one or more of the vectors produce out-of-range impedance values, ICD 16 may apply additional pacing pulses and/or selective different stimulation vectors the next time a pacing pulse or pair of pacing pulses are delivered.

In some cases, the FFEGM amplitude comparison and oversensed event remediation may be selectively activated when two or more consecutive FS events are detected and the patient is pacemaker-dependent, i.e., the patient has received pacing for more than 50% beats since the last sessions. Selective activation may avoid loss of battery longevity due to continuously evaluating the FFEGM amplitude. Another criteria may be used to deactivate the FFEGM analysis such as consecutive "normal" R-R intervals (e.g., 8 consecutive R-R intervals having lengths of greater than 500 milliseconds). By identifying oversensed conditions based on two or more events, ICD 16 identifies oversensed events and implements a remediation process to prevent inappropriate inhibition of pacing, thereby reducing the risk of syncope and asystole for the ICD patient.

Figure 11:
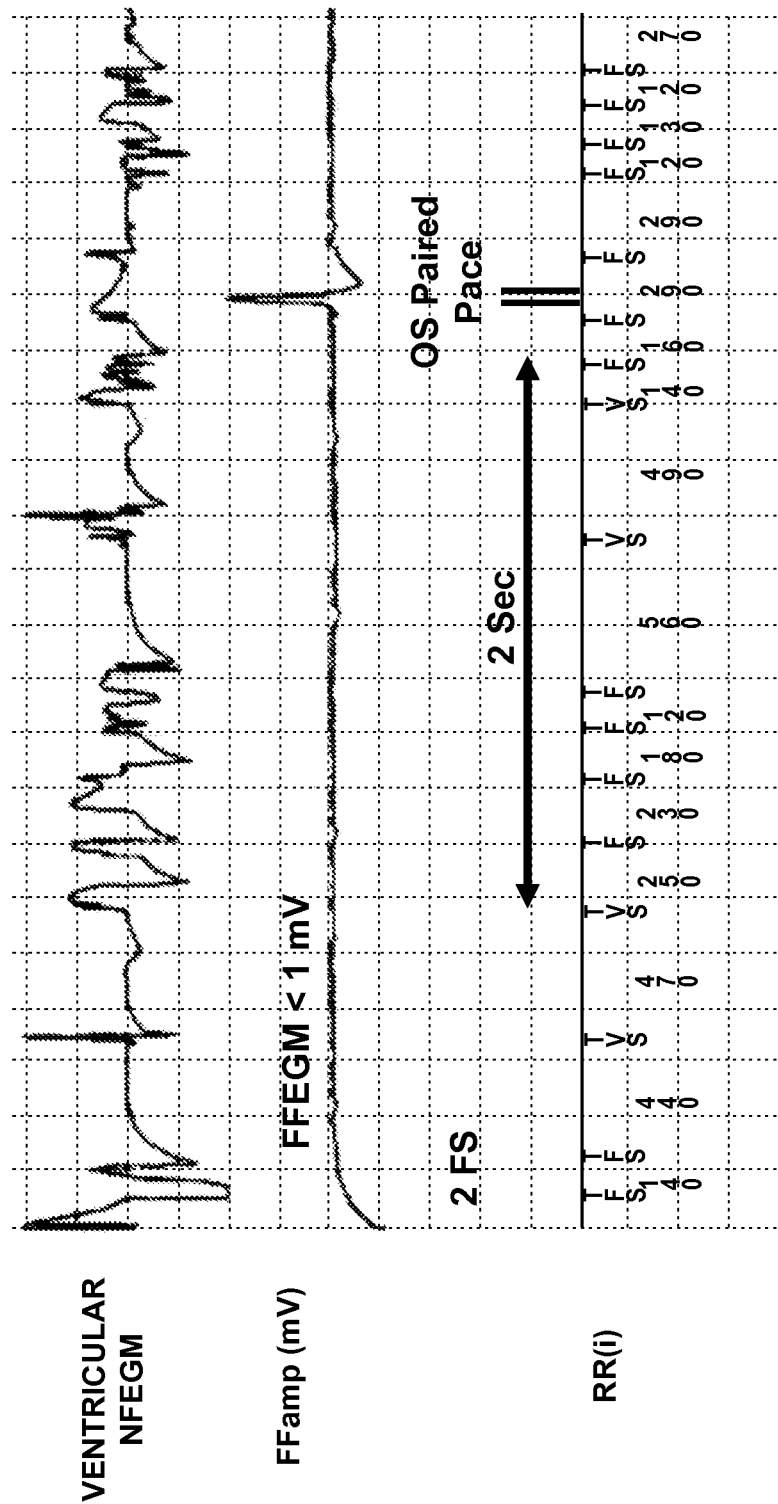
FIG. 11 is a graph illustrating an additional technique for identification and remediation of oversensed cardiac events using an FFEGM to permit delivery of a bradycardia pacing pulse and immediate backup pacing pulse.

FIG. 11 is a graph illustrating an additional technique for identification and remediation of oversensed cardiac events using an FFEGM to permit delivery of a bradycardia pacing pulse. More particularly, FIG. 11 shows a timeout-based remediation technique. In the example of FIG. 11, it is assumed that ICD 16 is a single-chamber ICD that does not have atrial sensing capabilities. However, the timeout-based remediation technique may be applied to apply a timeout period to ventricular events in single- or multi-chamber ICDs, or atrial events in multi-chamber ICDs.

For a single-chamber ICD, i.e., having only a right ventricular lead, the ICD 16 may trigger pacing if at least a minimum number of oversensed R wave events are identified in a specified period of time. The period of time may be, for example, a period of time following a previous non-oversensed R wave event. At the end of the period of time, the ICD may deliver a pacing pulse. Again, the ICD may, in some cases, deliver two or more pacing pulses in quick succession e.g., 5 to 100 milliseconds (ms) apart, using different stimulation vectors, and monitor impedance during each pacing pulse to evaluate the integrity of the stimulation path. In this manner, ICD 16 may reduce the likelihood that pacing may be inhibited due to oversensed events, and reduce the risk of syncope and asystole as a result of inhibited pacing.

The top line in FIG. 11 indicates the ventricular NFEGM signal indicating R waves. The second line indicates the ventricular FFEGM signal and amplitude (FFamp). The third line RR(i) provides marker channel data indicating ventricular R wave events, including ventricular sensed R waves (VS), ventricular fibrillation sensed (FS) events, and R-R intervals. As in the example of FIG. 10, if two or more consecutive FS events are detected, ICD 16 starts to compare the FFEGM amplitude coincident with those events to an applicable threshold amplitude. In the example of FIG. 11, after sensing the first two consecutive FS events, ICD 16 measures the amplitudes of the FFEGM signal for the next two VS events.

If the FFEGM amplitude at times corresponding to the two VS events is less than the threshold amplitude, 1 mV in FIG. 11, ICD 16 identifies an oversensing condition and activates the timeout period to run from the second VS event. If the FFEGM amplitude is not less than the threshold amplitude, ICD 16 does not identify an oversensed condition. When an oversensed condition is identified based on the FFEGM amplitude, ICD 16 delivers one or more pacing pulses in synchronization with the next sensed R wave (e.g., indicated by FS, TS, or VS) following the expiration of the timeout period. In the example of FIG. 11, the timeout period is two seconds, which corresponds to a lower rate limit for 30 beats per minute. ICD 16 may deliver the pacing pulse within a short period of time following the first sensed R wave (e.g., FS, TS, or VS) after the expiration of the timeout period, e.g., 5 to 100 ms following the sensed R wave. In FIG. 11, the FS event following expiration of the timeout period is the twelfth ventricular event.

In the example of FIG. 11, if the FFEGM amplitude is less than the threshold, indicating oversensing, the pacing pulse is delivered as a pair of pacing pulses (OS Paired Pace) in quick succession to provide overstimulation (OS) via multiple stimulation vectors. Again, the first pulse may be delivered via an electrode configuration formed, for example, by ring electrode 40 and tip electrode 42. A second, safety pace may be delivered through a second electrode configuration, such as coil electrode 62 and can electrode 58, or other electrode configurations such as configurations including electrodes on the left ventricular lead. Again, in addition to delivering multiple pacing pulses, the amplitudes of the pulses may be increased, in some implementations, when oversensed events are detected.

In the process described with reference to FIG. 11, as alternatives to FFEGM amplitude within a defined window of sampled voltages, or additionally, ICD 16 may consider slope, variability, or other characteristics. Another example characteristic may be a cumulative amplitude of the portions of the FFEGM signal corresponding to the FS events, in comparison to a particular threshold value. Again, ICD 16 may measure impedance on the stimulation vectors and, if one or more of the vectors produce out-of-range impedance values (e.g., Z>2000 ohms), ICD 16 may apply additional pacing pulses and/or selective different stimulation vectors the next time a pacing pulse or pair of pacing pulses are delivered.

As described with reference to FIG. 10, in the example of FIG. 11, the FFEGM amplitude comparison and oversensed event remediation may be selectively activated when two or more consecutive FS events are detected and the patient is pacemaker-dependent, i.e., the patient has received pacing for more than 50% beats since the last sessions. By identifying oversensed conditions based on two or more events, ICD 16 identifies oversensed events and implements a remediation process to prevent inappropriate inhibition of pacing, thereby reducing the risk of syncope and asystole for the ICD patient.

Although the techniques described with reference to FIG. 11 make use of ventricular events to trigger delivery of an OS paired pace following expiration of the timeout period, the timeout period may run from a previous atrial event and the OS paired paced (or single pulses in other cases) may be applied after the next atrial (AS, AP, or AR) following expiration the timer. Accordingly, timeout-based techniques for remediation of oversensing may rely on ventricular events or atrial events, or a combination of both in conjunction with a timeout period to time the delivery of one or more pacing pulses in the event ICD 16 detects an oversensing condition using the FFEGM amplitude. In general, for OS pacing, it may be desirable to deliver the second or subsequent pacing pulses within an applicable refractory period following the first pulse and to avoid further pacing within an applicable vulnerable period such as during a T wave.

The techniques described in this disclosure, including those attributed to ICD 16 or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete digital, analog or logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:
1. A method comprising:
acquiring a first cardiac signal via a first sense electrode configuration;
acquiring a second cardiac signal via a second sense electrode configuration;
detecting a plurality of cardiac events in the first cardiac signal;
measuring a plurality of intervals between the cardiac events detected in the first cardiac signal;
analyzing one or more characteristics of the second cardiac signal to determine whether at least one of the plurality of cardiac events detected in the first cardiac signal comprises an oversensed event;
identifying at least one oversensed event of the plurality of cardiac events in the first cardiac signal based on the analysis of the one or more characteristics of the second cardiac signal; and
controlling delivery of a cardiac electrical stimulation therapy to a patient based on the identification of at least one oversensed event by:
withholding a first interval of the plurality of intervals from a therapy delivery control module in response to identifying the at least one oversensed event causing the first interval to have been measured;
obtaining a summed interval by summing the first interval with one or more next intervals of the plurality of intervals until a last of the next intervals that is not between oversensed events; and
providing the summed interval to the therapy delivery control module for use in controlling delivery of the cardiac electrical stimulation therapy.

2. The method of claim 1, wherein controlling delivery of the cardiac electrical stimulation therapy further comprises:
detecting that the summed interval is greater than a threshold time interval; and
delivering pacing therapy to the patient in response to the detection that the summed interval is greater than the threshold time interval.

3. The method of claim 2, wherein delivering pacing therapy comprises:
delivering first pacing therapy via a first stimulation electrode configuration in response to the detection that the summed interval is greater than the threshold time interval; and
delivering second pacing therapy via a second stimulation electrode configuration in response to the detection that the summed interval is greater than the threshold time interval.

4. The method of claim 3, wherein the first stimulation electrode configuration comprises electrodes carried by a first lead implanted to deliver the first pacing therapy to a first chamber of the heart, and the second stimulation electrode configuration comprises electrodes carried by a second lead implanted to deliver the second pacing therapy to a second chamber of the heart.

5. The method of claim 3, further comprising measuring impedance values of at least one of the first and second stimulation electrode configurations.

6. The method of claim 1, wherein controlling delivery of the cardiac electrical stimulation therapy further comprises:
determining time intervals between the detected cardiac events that are not identified as oversensed events, wherein at least one of the time intervals includes the summed interval;
determining a count of a number of the time intervals that are shorter than a threshold time interval;
detecting that the count is greater than a threshold count; and
delivering at least one of cardioversion or defibrillation therapy to the patient in response to the detection that the count is greater than the threshold count.

7. The method of claim 1, wherein controlling delivery of the cardiac electrical stimulation therapy further comprises:
determining time intervals between the detected cardiac events that are not identified as oversensed events, wherein at least one of the time intervals includes the summed interval;
detecting that at least one of the time intervals is greater than a first threshold time interval;
delivering pacing therapy to the patient in response to the detection that at least one of the time intervals is greater than the first threshold time interval;
determining a count of a number of the time intervals that are shorter than a second threshold time interval;
detecting that the count is greater than a threshold count; and
delivering at least one of cardioversion or defibrillation therapy to the patient in response to the detection that the count is greater than the threshold count.

8. The method of claim 1, wherein the first cardiac signal is a near-field electrogram signal, the second cardiac signal is a far-field electrogram signal, the first sense electrode configuration comprises a tip electrode and a ring electrode carried by a ventricular lead, and the second sense electrode configuration comprises a coil electrode carried by the ventricular lead and a can electrode carried by a housing of an implantable medical device.

9. The method of claim 1, wherein identifying at least one oversensed event of the plurality of cardiac events in the first cardiac signal comprises identifying each of the cardiac events as an oversensed event if an amplitude of the second cardiac signal at a time substantially coincident with the respective cardiac event detected in the first cardiac signal is below a threshold amplitude.

10. The method of claim 1, wherein analyzing one or more characteristics of the second cardiac signal comprises determining whether an amplitude of the second cardiac signal at a time substantially coincident with the respective cardiac event detected in the first cardiac signal is below a threshold amplitude.

11. An implantable medical device comprising:
an electrical sensing module configured to acquire a first cardiac signal via a first sense electrode configuration, and to acquire a second cardiac signal via a second sense electrode configuration;
a stimulation module configured to deliver a cardiac electrical stimulation therapy to a patient via a plurality of stimulation electrodes;
a therapy delivery control module configured to control the stimulation module configured to deliver the cardiac electrical stimulation therapy; and
a processor configured to:
detect a plurality of cardiac events in the first cardiac signal;
measure a plurality of intervals between the plurality of cardiac events detected in the first cardiac signal;
analyze one or more characteristics of the second cardiac signal to determine whether at least one of the plurality of cardiac events detected in the first cardiac signal comprises an oversensed event; and
identify at least one oversensed event of the plurality of cardiac events in the first cardiac signal based on the analysis of the one or more characteristics of the second cardiac signal, and
control the stimulation module to deliver the cardiac electrical stimulation therapy to the patient based on the identification of at least one oversensed event by:
withholding a first interval of the plurality of intervals from the therapy delivery control module in response to identifying the at least one oversensed event causing the first interval to have been measured;
obtaining a summed interval by summing the first interval with one or more next intervals of the plurality of intervals until a last of the next intervals that is not between oversensed events; and
providing the summed interval to the therapy delivery control module for use in controlling delivery of the cardiac electrical stimulation therapy by the stimulation module.

12. The device of claim 11, wherein the therapy delivery control module is further configured to detect that the summed interval is greater than a threshold time interval, and to control the stimulation module to deliver pacing therapy to the patient in response to the detection that the summed interval is greater than the threshold time interval.

13. The device of claim 12, wherein the therapy delivery control module is further configured to control the stimulation module to deliver first pacing therapy via a first stimulation electrode configuration in response to the detection that the summed interval is greater than the threshold time interval, and deliver second pacing therapy via a second stimulation electrode configuration in response to the detection that the summed interval is greater than the threshold time interval.

14. The device of claim 13, further comprising the first stimulation electrode configuration and the second stimulation electrode configuration, wherein the first stimulation electrode configuration comprises electrodes carried by a first implantable lead to deliver the first pacing therapy to a first chamber of the heart, and the second stimulation electrode configuration comprises electrodes carried by a second lead implantable to deliver the second pacing therapy to a second chamber of the heart.

15. The device of claim 13, further comprising an impedance measurement module configured to measure impedance values of at least one of the first and second stimulation electrode configurations.

16. The device of claim 11, wherein the therapy delivery control module is further configured to:
   determine time intervals between the detected cardiac events that are not identified as oversensed events, wherein at least one of the time intervals includes the summed interval;
   determine a count of a number of the time intervals that are shorter than a threshold time interval;
   detect that the count is greater than a threshold count; and
   control the stimulation module to deliver at least one of cardioversion or defibrillation therapy to the patient in response to the detection that the count is greater than the threshold count.

17. The device of claim 11, wherein the therapy delivery control module is further configured to:
   determine time intervals between the detected cardiac events that are not identified as oversensed events, wherein at least one of the time intervals includes the summed interval;
   detect that at least one of the time intervals is greater than a first threshold time interval;
   deliver pacing therapy to the patient in response to the detection that one of the time intervals is greater than the first threshold time interval;
   determine a count of a number of the time intervals that are shorter than a second threshold time interval;
   detect that the count is greater than a threshold count; and
   deliver at least one of cardioversion or defibrillation therapy to the patient in response to the detection that the count is greater than the threshold count.

18. The device of claim 11, wherein the first cardiac signal is a near-field electrogram signal, the second cardiac signal is a far-field electrogram signal, and the device further comprises a ventricular lead, the first sense electrode configuration, and the second sense electrode configuration, wherein the first sense electrode configuration comprises a tip electrode and a ring electrode carried by the ventricular lead, and the second sense electrode configuration comprises a coil electrode carried by the ventricular lead and a can electrode carried by a housing of the implantable medical device.

19. The device of claim 11, wherein the processor is configured to identify each of the cardiac events as an oversensed event if an amplitude of the second cardiac signal at a time substantially coincident with the respective cardiac event detected in the first cardiac signal is below a threshold amplitude.

20. The device of claim 11, wherein the processor is further configured to determine whether an amplitude of the second cardiac signal at a time substantially coincident with the respective cardiac event detected in the first cardiac signal is below a threshold amplitude.

21. An implantable medical device comprising:
   means for acquiring a first cardiac signal via a first sense electrode configuration;
   means for acquiring a second cardiac signal via a second sense electrode configuration;
   means for detecting a plurality of cardiac events in the first cardiac signal;
   means for measuring a plurality of intervals between the plurality of cardiac events detected in the first cardiac signal;
   means for analyzing one or more characteristics of the second cardiac signal to determine whether at least one of the plurality of cardiac events detected in the first cardiac signal comprises an oversensed event;
   means for identifying at least one oversensed event of the plurality of cardiac events in the first cardiac signal based on the analysis of the whether one or more characteristics of the second cardiac; and
   means for controlling delivery of a cardiac electrical stimulation therapy to a patient based on the identification of at least one oversensed event by:
      withholding a first interval of the plurality of intervals from a therapy control module in response to identifying the at least one oversensed event causing the first interval to have been measured;
      obtaining a summed interval by summing the first interval with one or more next intervals of the plurality of intervals until a last of the next intervals that is not between oversensed events; and
      providing the summed interval to the therapy delivery control module for use in controlling delivery of the cardiac electrical stimulation therapy.

22. The device of claim 21, wherein the means for controlling delivery comprises:
   means for detecting that the summed interval is greater than a threshold time interval; and
   means for delivering pacing therapy to the patient in response to the detection that the summed interval is greater than the threshold time interval.

23. The device of claim 22, wherein the means for delivering pacing therapy comprises:
   means for delivering first pacing therapy via a first stimulation electrode configuration in response to the detection that the summed interval is greater than the threshold time interval; and
   means for delivering second pacing therapy via a second stimulation electrode configuration in response to the detection that the summed interval is greater than the threshold time interval.

24. The device of claim 23, wherein the first stimulation electrode configuration comprises electrodes carried by a first lead implantable to deliver the first pacing therapy to a first chamber of the heart, and the second stimulation electrode configuration comprises electrodes carried by a second lead implantable to deliver the second pacing therapy to a second chamber of the heart.

25. The device of claim 23, further comprising means for measuring impedance values of at least one of the first and second stimulation electrode configurations.

26. The device of claim 21, wherein the means for controlling delivery of the cardiac electrical stimulation therapy further comprises:
    means for determining time intervals between the detected cardiac events that are not identified as oversensed events, wherein at least one of the time intervals includes the summed interval;
    means for determining a count of a number of the time intervals that are shorter than a threshold time interval;
    means for detecting that the count is greater than a threshold count; and
    means for delivering at least one of cardioversion or defibrillation therapy to the patient in response to the detection that the count is greater than the threshold count.

27. The device of claim 21, wherein the means for controlling delivery of the cardiac electrical stimulation therapy further comprises:
    means for determining time intervals between the detected cardiac events that are not identified as oversensed events, wherein at least one of the time intervals includes the summed interval;
    means for detecting that at least one of the time intervals is greater than a first threshold time interval;
    means for delivering pacing therapy to the patient in response to the detection that at least one of the time intervals is greater than the first threshold time interval;
    means for determining a count of a number of the time intervals that are shorter than a second threshold time interval;
    means for detecting that the count is greater than a threshold count; and
    means for delivering at least one of cardioversion or defibrillation therapy to the patient in response to the detection that the count is greater than the threshold count.

28. The device of claim 21, wherein the first cardiac signal is a near-field electrogram signal, the second cardiac signal is a far-field electrogram signal, the first sense electrode configuration comprises a tip electrode and a ring electrode carried by a ventricular lead, and the second sense electrode configuration comprises a coil electrode carried by the ventricular lead and a can electrode carried by a housing of the implantable medical device.

29. The device of claim 21, wherein the means for identifying at least one oversensed event of the plurality of cardiac events in the first cardiac signal comprises means for identifying each of the cardiac events as an oversensed event if an amplitude of the second cardiac signal at a time substantially coincident with the respective cardiac event detected in the first cardiac signal is below a threshold amplitude.

30. The device of claim 21, wherein the means for analyzing one or more characteristics of the second cardiac signal comprises means for determining whether an amplitude of the second cardiac signal at a time substantially coincident with the respective cardiac event detected in the first cardiac signal is below a threshold amplitude.

31. A non-transitory computer-readable storage medium comprising instructions that, when executed by a processor in an implantable medical device, cause the processor to:
    detect a plurality of cardiac events in a first cardiac signal acquired via a first sense electrode configuration;
    measure a plurality of intervals between the plurality of cardiac events detected in the first cardiac signal;
    analyze one or more characteristics of a second cardiac signal acquired via a second sense electrode configuration to determine whether at least one of the plurality of cardiac events detected in the first cardiac signal comprises an oversensed event;
    identify at least one oversensed event of the plurality of cardiac events in the first cardiac signal based on the analysis of the one or more characteristics of the second cardiac signal; and
    control a stimulation module to deliver a cardiac electrical stimulation therapy to a patient based on the identification of at least one oversensed event by:
        withholding a first interval of the plurality of intervals from a therapy delivery control module in response to identifying at least one oversensed event causing the first interval to have been measured;
        obtaining a summed interval by summing the first interval with one or more next intervals of the plurality of intervals until a last of the next intervals that is not between oversensed events; and
        providing the summed interval to the therapy delivery control module for use in controlling delivery of the cardiac electrical stimulation therapy.

32. The computer-readable storage medium of claim 31, wherein the instructions cause the processor to:
    detect that the summed interval is greater than a threshold time interval; and
    control the stimulation module to deliver pacing therapy to the patient in response to the detection that the summed interval is greater than the threshold time interval.

33. The computer-readable storage medium of claim 32, wherein the instructions cause the processor to:
    control the stimulation module to deliver first pacing therapy via a first stimulation electrode configuration in response to the detection that the summed interval is greater than the threshold time interval; and
    control the stimulation module to deliver second pacing therapy via a second stimulation electrode configuration in response to the detection that the summed interval is greater than the threshold time interval.

34. The computer-readable storage medium of claim 33, wherein the instructions cause the processor to obtain measured impedance values of at least one of the first and second stimulation electrode configurations.

35. The computer-readable storage medium of claim 31, wherein the instructions cause the processor to:
    determine time intervals between the detected cardiac events that are not identified as oversensed events, wherein at least one of the time intervals includes the summed interval;
    determine a count of a number of the time intervals that are shorter than a threshold time interval;
    detect that the count is greater than a threshold count; and
    control the stimulation module to deliver at least one of cardioversion or defibrillation therapy to the patient in response to the detection that the count is greater than the threshold count.

36. The computer-readable storage medium of claim 31, wherein the instructions cause the processor to:
    determine time intervals between the detected cardiac events that are not identified as oversensed events, wherein at least one of the time intervals includes the summed interval;
    detect that at least one of the time intervals is greater than a first threshold time interval;
    control the stimulation module to deliver pacing therapy to the patient in response to the detection that one of the time intervals is greater than the first threshold time interval;

determine a count of a number of the time intervals that are shorter than a second threshold time interval;
detect that the count is greater than a threshold count; and
control the stimulation module to deliver at least one of cardioversion or defibrillation therapy to the patient in response to the detection that the count is greater than the threshold count.

37. The computer-readable storage medium of claim 31, wherein the first cardiac signal is a near-field electrogram signal, the second cardiac signal is a far-field electrogram signal, the first sense electrode configuration comprises a tip electrode and a ring electrode carried by a ventricular lead, and the second sense electrode configuration comprises a coil electrode carried by the ventricular lead and a can electrode carried by a housing of the implantable medical device.

38. The computer-readable storage medium of claim 31, wherein the instructions cause the processor to identify each of the cardiac events as an oversensed event if an amplitude of the second cardiac signal at a time substantially coincident with the respective cardiac event detected in the first cardiac signal is below a threshold amplitude.

39. The computer-readable storage medium of claim 31, wherein the instructions cause the processor to determine whether an amplitude of the second cardiac signal at a time substantially coincident with the respective cardiac event detected in the first cardiac signal is below a threshold amplitude.

* * * * *